(12) United States Patent
Patel et al.

(10) Patent No.: US 9,381,200 B2
(45) Date of Patent: *Jul. 5, 2016

(54) NITROGEN CONTAINING COMPOUNDS

(71) Applicant: WOCKHARDT LIMITED, Aurangabad (IN)

(72) Inventors: Mahesh Vithalbhai Patel, Aurangabad (IN); Prasad Keshav Deshpande, Aurangabad (IN); Satish Bhawasar, Aurangabad (IN); Sachin Bhagwat, Aurangabad (IN); Mohammad Alam Jafri, Aurangabad (IN); Amit Mishra, Lucknow (IN); Laxmikant Pavase, Ahmednagar (IN); Sunil Gupta, Kota (IN); Rajesh Kale, Amravati (IN); Sanjeev Joshi, Aurangabad (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,048

(22) Filed: Jul. 9, 2015

(65) Prior Publication Data

US 2015/0328201 A1 Nov. 19, 2015

Related U.S. Application Data

(63) Continuation of application No. 14/609,704, filed on Jan. 30, 2015, now Pat. No. 9,132,133, which is a continuation of application No. 14/452,652, filed on Aug. 6, 2014, now Pat. No. 8,987,297, which is a continuation of application No. 14/294,364, filed on Jun. 3, 2014, now Pat. No. 8,853,197, which is a continuation of application No. 14/111,592, filed as application No. PCT/IB2012/054290 on Aug. 24, 2012, now Pat. No. 8,822,450.

(30) Foreign Application Priority Data

Aug. 27, 2011 (IN) .......................... 2412/MUM/2011

(51) Int. Cl.

| | |
|---|---|
| A61K 31/439 | (2006.01) |
| A61K 31/5377 | (2006.01) |
| A61K 31/4545 | (2006.01) |
| A61K 31/167 | (2006.01) |
| A61K 31/407 | (2006.01) |
| A61K 31/427 | (2006.01) |
| A61K 31/429 | (2006.01) |
| A61K 31/43 | (2006.01) |
| A61K 31/496 | (2006.01) |
| A61K 31/529 | (2006.01) |
| A61K 31/542 | (2006.01) |
| A61K 31/546 | (2006.01) |
| C07D 471/08 | (2006.01) |
| A61K 45/06 | (2006.01) |

(52) U.S. Cl.
CPC ........... *A61K 31/5377* (2013.01); *A61K 31/167* (2013.01); *A61K 31/407* (2013.01); *A61K 31/427* (2013.01); *A61K 31/429* (2013.01); *A61K 31/43* (2013.01); *A61K 31/439* (2013.01); *A61K 31/4545* (2013.01); *A61K 31/496* (2013.01); *A61K 31/529* (2013.01); *A61K 31/542* (2013.01); *A61K 31/546* (2013.01); *A61K 45/06* (2013.01); *C07D 471/08* (2013.01)

(58) Field of Classification Search
CPC .................................................... A61K 31/439
USPC ............................................................ 514/300
See application file for complete search history.

(56) References Cited

U.S. PATENT DOCUMENTS

2010/0093784 A1 4/2010 Ledoussal et al.

FOREIGN PATENT DOCUMENTS

WO WO 2009091856 A2 7/2009

*Primary Examiner* — Niloofar Rahmani
(74) *Attorney, Agent, or Firm* — Bio Intellectual Property Services LLC (Bio IPS); O. (Sam) Zaghmout

(57) ABSTRACT

Compounds of Formula (I), their preparation and use in preventing or treating bacterial infection is disclosed.

Formula (I)

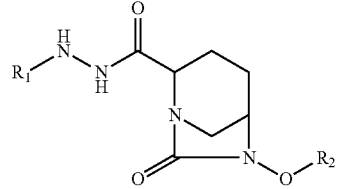

9 Claims, No Drawings

NITROGEN CONTAINING COMPOUNDS

RELATED PATENT APPLICATIONS

This application is a continuation of Ser. No 14/609,704, filed on Jan. 30, 2015, which is a continuation of U.S. Pat. No. 8,987,297 filed as Ser. No 14/452,652, filed on Aug. 6, 2014, which is a continuation of U.S. Pat. No. 8,853,197 filed as Ser. No. 14/294,364 on Jun. 3, 2014, which is a continuation of U.S. Pat. No. 8,822,450 filed as Ser. No. 14/111,592 on Dec. 20, 2013, which entered the National Phase of Serial No. PCT/IB12/54290, filed Aug. 24, 2012, which claims the benefit of Indian Provisional Patent Application No. 2412/MUM/ 2011 filed on Aug. 27, 2011, the disclosures of which are incorporated herein by reference in its entirety as if fully rewritten herein. All references including patents, patent applications, and literature cited in the specification are expressly incorporated herein by reference in their entirety.

FIELD OF THE INVENTION

The invention relates to nitrogen containing compounds, their preparation and their use in preventing and/or treating bacterial infections.

BACKGROUND OF THE INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistance. Coates et al. (Br. J. Pharmacol. 2007; 152(8), 1147-1154.) have reviewed novel approaches to developing new antibiotics. However, the development of new antibacterial agents is a challenging task. For example, Gwynn et al. (Annals of the New York Academy of Sciences, 2010, 1213: 5-19) have reviewed the challenges in the discovery of antibacterial agents.

Several antibacterial agents have been described in the prior art (for example, see PCT International Application Nos. PCT/US2010/060923, PCT/EP2010/067647, PCT/US2010/052109, PCT/US2010/048109, PCT/GB2009/050609, PCT/EP2009/056178 and PCT/US2009/041200). However, there remains a need for potent antibacterial agents for preventing and/or treating bacterial infections, including those caused by bacteria that are resistant to known antibacterial agents.

The inventors have surprisingly discovered nitrogen containing compounds with antibacterial properties.

SUMMARY OF THE INVENTION

Accordingly there are provided nitrogen containing compounds, methods for preparation of these compounds, pharmaceutical compositions comprising these compounds, and method for preventing or treating bacterial infection in a subject using these compounds.

In one general aspect, there are provided compounds of Formula (I):

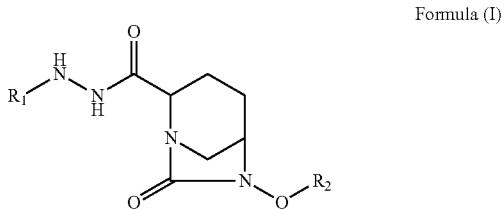

Formula (I)

or a stereoisomer or a pharmaceutically acceptable salt thereof;

wherein:

$R_1$ is:
(a) hydrogen,
(b) $(CO)_n—R_3$,
(c) $COOR_4$, or
(d) $COCH_2COR_3$ n is 0, 1 or 2;

$R_2$ is:
(a) $SO_3M$,
(b) $SO_2NH_2$,
(c) $PO_3M$,
(d) $CH_2COOM$,
(e) $CF_2COOM$,
(f) $CHFCOOM$, or
(g) $CF_3$;

M is hydrogen or a cation;

$R_3$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, $NR_5CONR_6R_7$, heterocyclyl, heteroaryl, cycloalkyl or aryl,
(c) CN,
(d) $NR_6R_7$,
(e) $CONR_6R_7$,
(f) $NHCONR_6R_7$,
(g) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(h) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, $NHC(NH)NR_6R_7$, or $NHCONR_6R_7$,
(i) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(j) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(k) cycloalkyl substituted with $C_1$-$C_6$ alkyl wherein $C_1$-$C_6$ alkyl is further substituted with one or more substituents independently selected from $OR_5$, $NR_6R_7$, halogen, CN, or $CONR_6R_7$, or (l) $OR_8$;

$R_4$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(d) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(e) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$, or
(f) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$;

$R_5$ and $R_8$ are each independently:
(a) hydrogen, or
(b) $C_1$-$C_6$ alkyl optionally substituted with one or more substituents independently selected from halogen, CN, $CONR_6R_7$, $NR_6R_7$, heterocyclyl, heteroaryl, cycloalkyl or aryl;

$R_6$ and $R_7$ are each independently:
(a) hydrogen,
(b) $C_1$-$C_6$ alkyl optionally substituted with one or more substituents independently selected from halogen, $OR_5$, CN, $COOR_5$, $CONR_5R_8$, $NR_5R_8$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(d) heterocyclyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(e) heteroaryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(f) cycloalkyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$, or
(g) $R_6$ and $R_7$ are joined together to form a four to seven member ring.

In another general aspect, there are provided pharmaceutical compositions comprising a compound of Formula (I), or a stereoisomer or a pharmaceutically acceptable salt thereof.

In another general aspect, there is provided a method for preventing or treating bacterial infection in a subject, said method comprising administering to said subject a pharmaceutically effective amount of a compound of Formula (I) or a stereoisomer or a pharmaceutically acceptable salt thereof.

In another general aspect, there is provided a method for preventing or treating a bacterial infection in a subject, said infection being caused by bacteria producing one or more beta-lactamase enzymes, wherein the method comprises administering to said subject a pharmaceutically effective amount of a compound of Formula (I) or a stereoisomer or a pharmaceutically acceptable salt thereof.

In another general aspect, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable salt thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a compound of Formula (I) or a stereoisomer or a pharmaceutically acceptable salt thereof.

In another general aspect, there are provided pharmaceutical compositions comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In another general aspect, there are provided pharmaceutical compositions comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In another general aspect, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there are provided methods for increasing antibacterial effectiveness of a antibacterial agent in a subject, said method comprising co-administering said antibacterial agent or a pharmaceutically acceptable derivative thereof with a pharmaceutically effective amount of a compound of Formula (I) or a stereoisomer or a pharmaceutically acceptable salt thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety.

The inventors have surprisingly discovered novel nitrogen containing compounds having antibacterial properties.

The term "$C_1$-$C_6$ alkyl" as used herein refers to branched or unbranched acyclic hydrocarbon radical with 1 to 6 carbon atoms. Typical, non-limiting examples of "$C_1$-$C_6$ alkyl" include methyl, ethyl, n-propyl, iso-propyl, n-butyl, iso-butyl, tert-butyl, n-pentyl, iso-pentyl, n-hexyl and the like. The "$C_1$-$C_6$ alkyl" may be unsubstituted, or substituted with one or more substituents. Typical, non-limiting examples of such substituents include halogen, alkoxy, CN, COOH, $CONH_2$, OH, —$NH_2$, —$NHCOCH_3$, cycloalkyl, heterocyclyl, heteroaryl, aryl and the like.

The term "cycloalkyl" as used herein refers to three to seven member cyclic hydrocarbon radicals. The cycloalkyl group optionally incorporates one or more double or triple bonds, or a combination of double bonds and triple bonds, but which is not aromatic. Typical, non-limiting examples of cycloalkyl groups include cyclopropane, cyclobutane, cyclopentane, cyclohexane, and cycloheptane. The cycloalkyl may be unsubstituted, or substituted with one or more substituents. Typical, non-limiting examples of such substituents include $C_1$-$C_6$ alkyl, halogen, alkoxy, CN, COOH, $CONH_2$, OH, NH$_2$, NHCOCH$_3$, heterocyclyl, heteroaryl, aryl, SO$_2$-alkyl, SO$_2$-aryl, OSO$_2$-alkyl, -OSO$_2$-aryl and the like.

The term "heterocyclyl" as used herein refers to four to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting examples of heterocycloalkyl groups include azetidine, pyrrolidine, 2-oxo-pyrrolidine, imidazolidin-2-one, piperidine, oxazine, thiazine, piperazine, piperazin-2,3-dione, morpholine, thiamorpholine, azapane, and the like. The heterocycloalkyl may be unsubstituted, or substituted with one or more substituents. Typical, non-limiting examples of such substituents include C$_1$-C$_6$ alkyl, halogen, alkoxy, CN, COOH, CONH$_2$, OH, NH$_2$, NHCOCH$_3$, heterocyclyl, heteroaryl, aryl, SO$_2$-alkyl, SO$_2$-aryl, OSO$_2$-alkyl, OSO$_2$-aryl and the like.

The term "aryl" as used herein refers to a monocyclic or polycyclic aromatic hydrocarbon. Typical, non-limiting examples of aryl groups include phenyl, naphthyl, anthracenyl, fluorenyl, phenanthrenyl, and the like. The aryl group may be unsubstituted, or substituted with one or more substituents. Typical, non-limiting examples of such substituents include C$_1$-C$_6$ alkyl, halogen, alkoxy, CN, COOH, CONH$_2$, OH, NH$_2$, NHCOCH$_3$, heterocyclyl, heteroaryl, aryl, SO$_2$-alkyl, SO$_2$-aryl, OSO$_2$-alkyl, OSO$_2$-aryl and the like.

The term "heteroaryl" as used herein refers to a monocyclic or polycyclic aromatic hydrocarbon group wherein one or more carbon atoms have been replaced with heteroatoms selected from nitrogen, oxygen, and sulfur. If the heteroaryl group contains more than one heteroatom, the heteroatoms may be the same or different. Typical, non-limiting example of heteroaryl groups include 1,2,4-oxadiazol, 1,3,4-oxadiazol, 1,3,4-thiadiazol, 1,2,3,4-tetrazol, 1,3-oxazol, 1,3-thiazole, pyridine, pyrimidine, pyrazine, pyridazine, furan, pyrrol, thiophene, imidazole, pyrazole, benzofuran, benzothiophene, benzimidazole, benzoxazole, benzothiazole, thiazole, and the like. The heteroaryl group may be unsubstituted, or substituted with one or more substituents. Typical, non-limiting examples of such substituents include C$_1$-C$_6$ alkyl, halogen, alkoxy, CN, COOH, CONH$_2$, OH, NH$_2$, NHCOCH$_3$, heterocyclyl, heteroaryl, aryl, SO$_2$-alkyl, SO$_2$-aryl, OSO$_2$-alkyl, OSO$_2$-aryl and the like.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, all geometric and positional isomers (including cis and trans-forms) as well as mixtures thereof, are also embraced within the scope of the invention. In general, a reference to a compound is intended to cover its stereoisomers and mixture of various stereoisomers.

The term "optionally substituted" as used herein means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (J. Pharmaceutical Sciences, 66: 1-19 (1977)), incorporated herein by reference in its entirety, describes various pharmaceutically acceptable salts in details.

In general, the compounds according to the invention contain basic (e.g. nitrogen atoms) as well as acid moieties (e.g. compounds of Formula (I) wherein M is hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid, or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional groups capable of being converted into salt, each such functional group may be converted to salt independently. For example, in case of compounds containing two basic nitrogen atoms, one basic nitrogen can form salt with one acid while the other basic nitrogen can form salt with another acid. Some compounds according to the invention contain both, acidic as well as basic moieties, and thus can form inner salts or corresponding zwitterions. In general, all pharmaceutically acceptable salt forms of compounds of Formula (I) according to invention including acid addition salts, base addition salts, zwitterions or the like are contemplated to be within the scope of the present invention and are generically referred to as pharmaceutically acceptable salts.

The term "halogen" or "halo" as used herein refers to chlorine, bromine, fluorine, or iodine.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to normal flora, which is not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In case of a pharmaceutical composition comprising more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to prevent or treat the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to a compound or material used to facilitate administration of a compound, including for example, to increase the solubility of the compound. Typical, non-limiting examples of solid carriers include, starch, lactose, dicalcium phosphate, sucrose, and kaolin and so on. Typical, non-limiting examples of liquid carriers include, sterile water, saline, buffers, non-ionic surfactants, and edible oils such as oil, peanut and sesame oils and so on. In addition, various adjuvants commonly used in the art may be included. These and other such compounds are described in the literature, for example, in the Merck Index (Merck & Company, Rahway, N.J.). Considerations for inclusion of various components in pharmaceutical compositions are described, for example, in Gilman et al. (Eds.) (1990); Goodman and Gilman's: The Pharmacological Basis of Therapeutics, 8th Ed., Pergamon Press., which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "pharmaceutically acceptable derivative" as used herein refers to and includes any pharmaceutically acceptable salt, pro-drugs, metabolites, esters, ethers, hydrates, polymorphs, solvates, complexes, enantiomers or adducts of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salt, pro-drugs, metabolites, esters, ethers, hydrates, polymorphs, solvates, complexes, enantiomers or adducts) which, upon administration to a subject, is capable of providing (directly or indirectly) the antibacterial compound.

In general, the term "cation" includes Na, K, Mg, Ca, $NH_4^+$, $(CH_3CH_2)_3N^+$ etc.

In one general aspect, there are provided compounds of Formula (I):

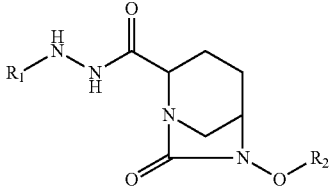

Formula (I)

or a stereoisomer or a pharmaceutically acceptable salt thereof;
wherein:
$R_1$ is:
(a) hydrogen,
(b) $(CO)_n$—$R_3$,
(c) $COOR_4$, or
(d) $COCH_2COR_3$
n is 0, 1 or 2;
$R_2$ is:
(a) $SO_3M$,
(b) $SO_2NH_2$,
(c) $PO_3M$,
(d) $CH_FCOOM$,
(e) $CF_2COOM$,
(f) CHFCOOM, or
(g) $CF_3$;
M is hydrogen or a cation;
$R_3$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, $NR_5CONR_6R_7$, heterocyclyl, heteroaryl, cycloalkyl or aryl,
(c) CN,
(d) $NR_6R_7$,
(e) $CONR_6R_7$,
(f) $NHCONR_6R_7$,
(g) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(h) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, $NHC(NH)NR_6R_7$, or $NHCONR_6R_7$,
(i) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(j) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(k) cycloalkyl substituted with $C_1$-$C_6$ alkyl wherein $C_1$-$C_6$ alkyl is further substituted with one or more substituents independently selected from $OR_5$, $NR_6R_7$, halogen, CN, or $CONR_6R_7$, or
(l) $OR_8$;
$R_4$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(d) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(e) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$, or
(f) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$;
$R_5$ and $R_8$ are each independently:
(a) hydrogen, or
(b) $C_1$-$C_6$ alkyl optionally substituted with one or more substituents independently selected from halogen, CN, $CONR_6R_7$, $NR_6R_7$, heterocyclyl, heteroaryl, cycloalkyl or aryl;
$R_6$ and $R_7$ are each independently:
(a) hydrogen,
(b) $C_1$-$C_6$ alkyl optionally substituted with one or more substituents independently selected from halogen, $OR_5$, CN, $COOR_5$, $CONR_5R_8$, $NR_5R_8$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(d) heterocyclyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(e) heteroaryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(f) cycloalkyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$, or
(g) R6 and $R_7$ are joined together to form a four to seven member ring.

Typical non-limiting examples of compounds according to the invention include:
trans-sulfuric acid mono-[2-(N'—[(S)-pyrrolidin-2-carbonyl]-hydrazinocarbonyl)-7-oxo-1,6-diaza-bicyclo[3.2.1]oct-6-yl]ester;
trans-sulfuric acid mono-[2-(N'—((R)-piperidin-3-carbonyl)-hydrazinocarbonyl)-7-oxo-1,6-diaza-bicyclo[3.2.1]oct-6-yl]ester;
trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester;
trans-{7-oxo-2-[N'—((R)-piperidin-3-carbonyl)-hydrazinocarbonyl]-1,6-diaza-bicyclo[3.2.1]-oct-6-yloxy}-acetic acid;

trans-difluoro-{7-oxo-2-[N'—((R)-piperidin-3-carbonyl)-hydrazinocarbonyl]-1,6-diaza-bicyclo[3.2.1]-oct-6-yloxy}-acetic acid;

trans-sulfuric acid mono-[2-hydrazinocarbonyl-7-oxo-1,6-diaza-bicyclo[3.2.1]oct-6-yl]ester;

trans-sulfuric acid mono-[2-(N'-(amino-acetyl)-hydrazinocarbonyl)-7-oxo-1,6-diaza-bicyclo[3.2.1]oct-6-yl]ester;

trans-sulfuric acid mono-[2-(N'-(3-amino-propioyl)-hydrazinocarbonyl)-7-oxo-1,6-diaza-bicyclo[3.2.1]oct-6-yl]ester;

trans-sulfuric acid mono-[2-(N'-(4-amino-butanoyl)-hydrazinocarbonyl)-7-oxo-1,6-diaza-bicyclo[3.2.1]oct-6-yl]ester;

trans-sulfuric acid mono-[2-(N'4(2S)-2-amino-3-hydroxy-propioyl)-hydrazinocarbonyl)-7-oxo-1,6-diaza-bicyclo[3.2.1]oct-6-yl]ester;

trans-sulfuric acid mono-[2-(N'-[(2S,4S)-4-fluoro-pyrrolidin-2-carbonyl]-hydrazinocarbonyl)-7-oxo-1,6-diaza-bicyclo[3.2.1]oct-6-yl]ester;

trans-sulfuric acid mono-[2-(N'-[(2S,4R)-4-methoxy-pyrrolidin-2-carbonyl]-hydrazinocarbonyl)-7-oxo-1,6-diaza-bicyclo[3.2.1]oct-6-yl]ester;

trans-sulfuric acid mono-[2-(N'-(piperidin-4-carbonyl)-hydrazinocarbonyl)-7-oxo-1,6-diaza-bicyclo[3.2.1]oct-6-yl]ester;

trans-sulfuric acid mono-[2-(N'—((RS)-piperidin-3-carbonyl)-hydrazinocarbonyl)-7-oxo-1,6-diaza-bicyclo[3.2.1]oct-6-yl]ester;

trans-sulfuric acid mono-[2-(N'—((S)-piperidin-3-carbonyl)-hydrazinocarbonyl)-7-oxo-1,6-diaza-bicyclo[3.2.1]oct-6-yl]ester;

trans-sulfuric acid mono-[2-(N'—((RS)-piperidin-2-carbonyl)-hydrazinocarbonyl)-7-oxo-1,6-diaza-bicyclo[3.2.1]oct-6-yl]ester;

trans-sulfuric acid mono-[2-(N'—((S)-piperidin-2-carbonyl)-hydrazinocarbonyl)-7-oxo-1,6-diaza-bicyclo[3.2.1]oct-6-yl]ester;

trans-sulfuric acid mono-[2-(N'—((R)-piperidin-2-carbonyl)-hydrazinocarbonyl)-7-oxo-1,6-diaza-bicyclo[3.2.1]oct-6-yl]ester;

trans-sulfuric acid mono-[2-(N'-(piperazin-4-yl-acetyl)-hydrazinocarbonyl)-7-oxo-1,6-diaza-bicyclo[3.2.1]oct-6-yl]ester;

trans-sulfuric acid mono-[2-(N'—((RS)-1-amino-1-phenyl-acetyl)-hydrazinocarbonyl)-7-oxo-1,6-diaza-bicyclo[3.2.1]oct-6-yl]ester;

trans-sulfuric acid mono-[2-(N'—((RS)-3-amino-butanoyl)-hydrazinocarbonyl)-7-oxo-1,6-diaza-bicyclo[3.2.1]oct-6-yl]ester;

trans-sulfuric acid mono-[2-(N'-(3-amino-2,2-dimethyl-propioyl)-hydrazinocarbonyl)-7-oxo-1,6-diaza-bicyclo[3.2.1]oct-6-yl]ester;

trans-sulfuric acid mono-[2-(N'-(1-aminomethyl-cyclopropan-1-carbonyl)-hydrazinocarbonyl)-7-oxo-1,6-diaza-bicyclo[3.2.1]oct-6-yl]ester;

trans-sulfuric acid mono-[2-(N'-(2-amino-4-carboxamido-butanoyl)-hydrazinocarbonyl)-7-oxo-1,6-diaza-bicyclo[3.2.1]oct-6-yl]ester;

trans-sulfuric acid mono-[2-(N'-(5-amino-pentanoyl)-hydrazinocarbonyl)-7-oxo-1,6-diaza-bicyclo[3.2.1]oct-6-yl]ester;

trans-sulfuric acid mono-[2-(N'-((2S)-2,6-diamino-hexanoyl)-hydrazinocarbonyl)-7-oxo-1,6-diaza-bicyclo[3.2.1]oct-6-yl]ester;

trans-sulfuric acid mono-[2-(N'-((2-aminoethoxy)-acetyl)-hydrazinocarbonyl)-7-oxo-1,6-diaza-bicyclo[3.2.1]oct-6-yl]ester;

trans-sulfuric acid mono-[2-(N'-[azetidin-3-carbonyl]-hydrazinocarbonyl)-7-oxo-1,6-diaza-bicyclo[3.2.1]oct-6-yl]ester;

trans-sulfuric acid mono-[2-(N'-[pyrrolidin-1-carbonyl]-hydrazinocarbonyl)-7-oxo-1,6-diaza-bicyclo[3.2.1]oct-6-yl]ester;

trans-sulfuric acid mono-[2-(N'—[(R)-pyrrolidin-2-carbonyl]-hydrazinocarbonyl)-7-oxo-1,6-diaza-bicyclo[3.2.1]oct-6-yl]ester;

trans-sulfuric acid mono-[2-(N'—[((S)-3-pyrrolidin-2-yl)-propionyl]-hydrazinocarbonyl)-7-oxo-1,6-diaza-bicyclo[3.2.1]oct-6-yl]ester;

trans-sulfuric acid mono-[2-(N'—[(RS)-pyrrolidin-3-carbonyl]-hydrazinocarbonyl)-7-oxo-1,6-diaza-bicyclo[3.2.1]oct-6-yl]ester;

trans-sulfuric acid mono-[2-(N'—[(S)-pyrrolidin-3-carbonyl]-hydrazinocarbonyl)-7-oxo-1,6-diaza-bicyclo[3.2.1]oct-6-yl]ester;

trans-sulfuric acid mono-[2-(N'-[(2S,4R)-4-hydroxy-pyrrolidin-2-carbonyl]-hydrazinocarbonyl)-7-oxo-1,6-diaza-bicyclo[3.2.1]oct-6-yl]ester;

trans-sulfuric acid mono-[2-(N'-[(2S,4S)-4-amino-pyrrolidin-2-carbonyl]-hydrazinocarbonyl)-7-oxo-1,6-diaza-bicyclo[3.2.1]oct-6-yl]ester;

trans-sulfuric acid mono-[2-(N'-[(2S,4S)-4-guanidino-pyrrolidin-2-carbonyl]-hydrazinocarbonyl)-7-oxo-1,6-diaza-bicyclo[3.2.1]oct-6-yl]ester;

trans-sulfuric acid mono-[2-(N'-[(RS)-3-piperidin-2-yl-propionyl]-hydrazinocarbonyl)-7-oxo-1,6-diaza-bicyclo[3.2.1]oct-6-yl]ester;

trans-sulfuric acid mono-[2-(N'—((RS)-piperazin-2-carbonyl)-hydrazinocarbonyl)-7-oxo-1,6-diaza-bicyclo[3.2.1]oct-6-yl]ester;

trans-sulfuric acid mono-[2-(N'—((S)-morpholin-3-carbonyl)-hydrazinocarbonyl)-7-oxo-1,6-diaza-bicyclo[3.2.1]oct-6-yl]ester;

trans-sulfuric acid mono-[2-(N'-(3-oxo-3-piperazin-1-yl-propionyl)-hydrazinocarbonyl)-7-oxo-1,6-diaza-bicyclo[3.2.1]oct-6-yl]ester;

trans-sulfuric acid mono-[2-(N'—((RS)-1-amino-1-pyridin-2-yl-acetyl)-hydrazinocarbonyl)-7-oxo-1,6-diaza-bicyclo[3.2.1]oct-6-yl]ester;

trans-sulfuric acid mono-[2-(N'-(2-amino-thiazol-4-carbonyl)-hydrazinocarbonyl)-7-oxo-1,6-diaza-bicyclo[3.2.1]oct-6-yl]ester;

Sodium salt of trans-sulfuric acid mono-[2-(N'-(cyano-acetyl)-hydrazinocarbonyl)-7-oxo-1,6-diaza-bicyclo[3.2.1]oct-6-yl]ester;

Sodium salt of trans-N'-(7-oxo-6-sulfooxy-1,6-diaza-bicyclo[3.2.1]octane-2-carboxylic acid)-hydrazinecarboxylic acid tert-butyl ester;

Sodium salt of trans-sulfuric acid mono-[2-(N'-(morpholin-4-yl-acetyl)-hydrazinocarbonyl)-7-oxo-1,6-diaza-bicyclo[3.2.1]oct-6-yl]ester;

Sodium salt of trans-sulfuric acid mono-[2-(N'-(6-carboxamido-pyridin-2-carbonyl)-hydrazinocarbonyl)-7-oxo-1,6-diaza-bicyclo[3.2.1]oct-6-yl]ester;

Sodium salt of trans-sulfuric acid mono-[2-(N'-(morpholin-4-oxo-carbonyl)-hydrazinocarbonyl)-7-oxo-1,6-diaza-bicyclo[3.2.1]oct-6-yl]ester;

Sodium salt of trans-sulfuric acid mono-[2-(N'—[(S)-1-carbamoyl-pyrrolidin-2-carbonyl]-hydrazinocarbonyl)-7-oxo-1,6-diaza-bicyclo [3.2.1]oct-6-yl]ester;

Sodium salt of trans-sulfuric acid mono-[2-(N'—[(2S,4S)-1-carbamoyl-4-fluoro-pyrrolidin-2-carbonyl]-hydrazinocarbonyl)-7-oxo-1,6-diaza-bicyclo[3.2.1]oct-6-yl]ester;

Sodium salt of trans-sulfuric acid mono-[2-(N'—[(S)-1-methanesulfonyl-pyrrolidin-2-carbonyl]-hydrazinocarbonyl)-7-oxo-1,6-diaza-bicyclo[3.2.1]oct-6-yl]ester;

Sodium salt of trans-sulfuric acid mono-[2-(N'-(cyano-dimethyl-acetyl)-hydrazinocarbonyl)-7-oxo-1,6-diaza-bicyclo[3.2.1]oct-6-yl]ester;

Sodium salt of trans-sulfuric acid mono-[2-(N'—[(S)-5-oxo-pyrrolidin-2-carbonyl]-hydrazinocarbonyl)-7-oxo-1,6-diaza-bicyclo[3.2.1]oct-6-yl]ester;

or a stereoisomer or a pharmaceutically acceptable salt thereof.

In general, the compounds of the invention can be prepared according to the following procedures (Scheme 1). A person of skills in the art would appreciate that the described methods can be varied or optimized further to provide the desired and related compounds. In the following procedures, all variables are as defined above.

As described in Scheme-1, trans-6-benzyloxy-7-oxo-1,6-diaza-bicyclo[3.2.1]-octane-2-carboxylic acid (1a), which is described in PCT International Publication No. WO 2009/091856, was reacted with corresponding acid hydrazides in presence of a suitable coupling agent such as EDC hydrochloride, or dicyclohexylcarbodiimide (DCC), in a solvent such as N,N dimethyl formamide; N,N dimethyl acetamide; 1,4 dioxane; chloroform; dichloromethane; or dichloroethane at a temperature ranging from −15° C. to 60° C. for about 1 to 24 hours to obtain intermediate compound (1b).

The intermediate compound (1b) was subjected for hydrogenolysis in presence of a suitable catalyst (e.g. 5% or 10% palladium on carbon, or 20% palladium hydroxide on carbon) in presence of a suitable hydrogen source (such as hydrogen gas, ammonium formate, cyclohexene) in a suitable solvent (such as methanol, ethanol, methanol-dichloromethane mixture, or N,N dimethyl formamide-dichloromethane mixture) at a temperature ranging from about 25° C. to 60° C. for about 1 to 14 hours to obtain intermediate compound (1c).

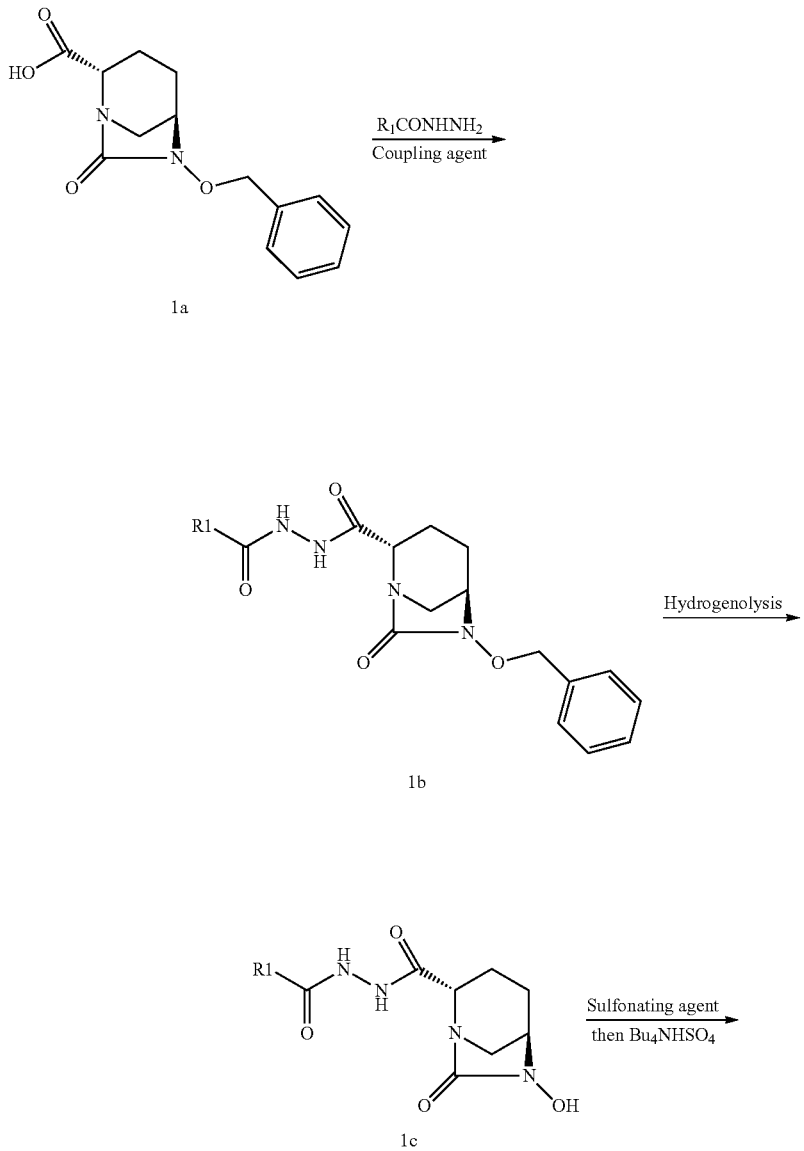

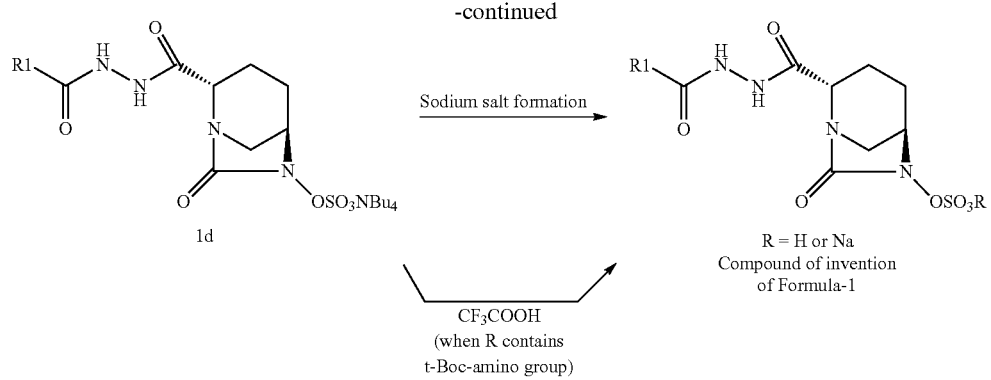

The intermediate compound (1c) was sulfonated by reacting it with a sulfonating reagent (such as sulfur trioxide-pyridine complex, or sulfur trioxide-N,N-dimethyl formamide complex) in a suitable solvent (such as pyridine, N,N-dimethyl formamide) at a temperature ranging from about 25° C. to 90° C. for about 1 to 24 hours to obtain pyridine salt of sulfonic acid which when treated with tetrabutyl ammonium sulfate provided terabutylammonium salt of sulfonic acid as an intermediate compound (1d).

Some compounds according to the invention were isolated as a zwitterions, by treating intermediate compound (1d) with trifluoroacetic acid, in a suitable solvent (such as dichloromethane, chloroform, or acetonitrile) at a temperature ranging from about −10° C. to 40° C. for about 1 to 14 hours, especially when R in intermediate compound (1d) contained tert-butoxycarbonyl protected amine function.

Some other compounds according to the invention were isolated as a corresponding sodium salt, by passing intermediate compound (1d) through sodium form of Aberlite 200C resin in a tetrahydrofuran-water mixture followed by evaporation of the solvent under vacuum.

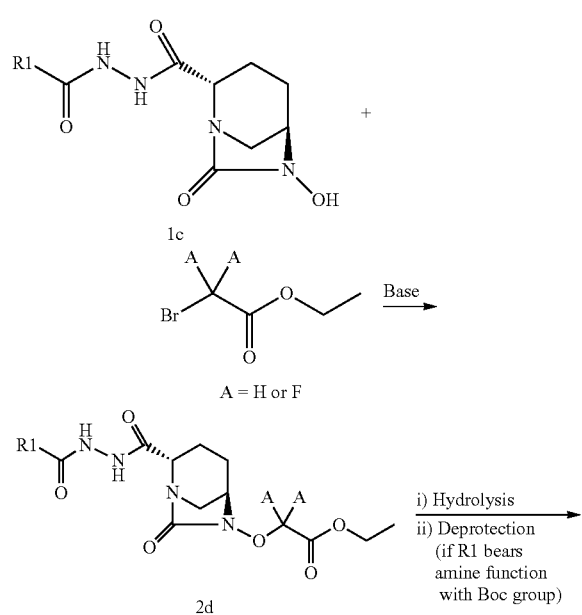

As described in Scheme-2, the hydroxyl intermediate (1c) obtained as per Scheme-1, was subjected for alkylation with alkylating agent (such as ethyl-bromoacetate, ethyl-fluoroacetate or ethyl-difluoroacetate) in presence of a base (such as potassium carbonate, diisopropylethylamine or triethylamine) in a suitable solvent (such as N,N dimethyl formamide, N,N dimethyl acetamide or N-methyl pyrrolidine) to provide O-alkylated compound (2d).

The compound (2d) was subjected for hydrolysis in presence of a base (such as lithium hydroxide or potassium hydroxide) in a suitable solvent (such as aqueous tetrahydrofuran, aquous dioxane) to provide compound of Formula (I) after pH adjustment.

Optionally, if $R_1$ bears amine function protected with Boc group, then it was removed in an additional step of deprotection by using a suitable deprotecting agent (such as trifluoroacetic acid or HF pyridine) in a solvent (such as dichloromethane, chloroform or acetonitrile) to provide compound of Formula (I).

In some embodiments, there are provided pharmaceutical compositions comprising a compound of Formula (I), or a stereoisomer or a pharmaceutically acceptable salt thereof.

In some other embodiments, there is provided a method for preventing or treating bacterial infection in a subject, said method comprising administering to said subject a pharmaceutically effective amount of a compound of Formula (I) or a stereoisomer or a pharmaceutically acceptable salt thereof.

In some embodiments, there is provided a method for preventing or treating a bacterial infection in a subject, said infection being caused by bacteria producing one or more beta-lactamase enzymes, wherein the method comprises administering to said subject a pharmaceutically effective amount of a compound of Formula (I) or a stereoisomer or a pharmaceutically acceptable salt thereof.

In some other embodiments, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable salt thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a compound of Formula (I) or a stereoisomer or a pharmaceutically acceptable salt thereof.

In some embodiments, there are provided pharmaceutical compositions comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In some other embodiments, there are provided pharmaceutical compositions comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some embodiments, there are provided pharmaceutical compositions comprising: (a) trans-sulfuric acid mono-[2-(N'—[(R)-piperidin-3-carbonyl]-hydrazinocarbonyl)-7-oxo-1,6-diaza-bicyclo[3.2.1]oct-6-yl] ester or a stereoisomer or a pharmaceutically acceptable salt thereof, and (b) sulbactam or a pharmaceutically acceptable derivative thereof.

In some other embodiments, there is provided a method for preventing or treating a bacterial infection in a subject, said method comprising administering to said subject a pharmaceutically effective amount of: (a) trans-sulfuric acid mono-[2-(N'—[(R)-piperidin-3-carbonyl]-hydrazinocarbonyl)-7-oxo-1,6-diaza-bicyclo[3.2.1]oct-6-yl]ester or a stereoisomer or a pharmaceutically acceptable salt thereof, and (b) sulbactam or a pharmaceutically acceptable derivative thereof.

In some other embodiments, there is provided a method for preventing or treating a bacterial infection in a subject, said infection being caused by bacteria producing one or more beta-lactamase enzymes, said method comprising administering to said subject a pharmaceutically effective amount of: (a) trans-sulfuric acid mono-[2-(N'—[(R)-piperidin-3-carbonyl]-hydrazinocarbonyl)-7-oxo-1,6-diaza-bicyclo[3.2.1]oct-6-yl]ester or a stereoisomer or a pharmaceutically acceptable salt thereof, and (b) sulbactam or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) trans-sulfuric acid mono-[2-(N'—[(R)-piperidin-3-carbonyl]-hydrazinocarbonyl)-7-oxo-1,6-diaza-bicyclo[3.2.1]oct-6-yl]ester or a stereoisomer or a pharmaceutically acceptable salt thereof, and (b) sulbactam or a pharmaceutically acceptable derivative thereof.

In some embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) trans-sulfuric acid mono-[2-(N'—[(R)-piperidin-3-carbonyl]-hydrazinocarbonyl)-7-oxo-1,6-diaza-bicyclo[3.2.1]oct-6-yl] ester or a stereoisomer or a pharmaceutically acceptable salt thereof, and (b) sulbactam or a pharmaceutically acceptable derivative thereof.

In some embodiments, there are provided pharmaceutical compositions comprising: (a) trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester or a stereoisomer or a pharmaceutically acceptable salt thereof, and (b) sulbactam or a pharmaceutically acceptable derivative thereof.

In some other embodiments, there is provided a method for preventing or treating a bacterial infection in a subject, said method comprising administering to said subject a pharmaceutically effective amount of: (a) trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester or a stereoisomer or a pharmaceutically acceptable salt thereof, and (b) sulbactam or a pharmaceutically acceptable derivative thereof.

In some other embodiments, there is provided a method for preventing or treating a bacterial infection in a subject, said infection being caused by bacteria producing one or more beta-lactamase enzymes, said method comprising administering to said subject a pharmaceutically effective amount of: (a) trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester or a stereoisomer or a pharmaceutically acceptable salt thereof, and (b) sulbactam or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester or a stereoisomer or a pharmaceutically acceptable salt thereof, and (b) sulbactam or a pharmaceutically acceptable derivative thereof.

In some embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester or a stereoisomer or a pharmaceutically acceptable salt thereof, and (b) sulbactam or a pharmaceutically acceptable derivative thereof.

In some embodiments, there are provided methods for increasing antibacterial effectiveness of a antibacterial agent in a subject, said method comprising co-administering said antibacterial agent or a pharmaceutically acceptable derivative thereof with a pharmaceutically effective amount of a compound of Formula (I) or a stereoisomer or a pharmaceutically acceptable salt thereof.

In some embodiments, the compositions and methods according to the invention use compounds of Formula (I) or a stereoisomer or a pharmaceutically acceptable salt thereof in combination with at least one antibacterial agent or a pharmaceutically acceptable derivative thereof. A wide variety of antibacterial agents can be used. Typical, non-limiting examples of antibacterial agents include one or more of antibacterial compounds generally classified as aminoglycosides, Ansamycins, Carbacephems, Cephalosporins, Cephamycins, Lincosamides, Lipopeptides, Macrolides, Monobactams, Nitrofurans, Penicillins, Polypeptides, Quinolones, Sulfonamides, Tetracyclines, Oxazolidinone and the like.

Typical, non-limiting examples of Aminoglycoside antibacterial agents include Amikacin, Gentamicin, Kanamycin, Neomycin, Netilmicin, Tobramycin, Paromomycin, Arbekacin, Streptomycin, Apramycin and the like.

Typical, non-limiting examples of Ansamycin antibacterial agents include Geldanamycin, Herbimycin and the like.

Typical, non-limiting examples of Carbacephem antibacterial agents include Loracarbef and the like.

Typical, non-limiting examples of Carbapenem antibacterial agents include Ertapenem, Doripenem, Imipenem, Meropenem and the like.

Typical, non-limiting examples of Cephalosporin and Cephamycin antibacterial agents include Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cephamycin, Cefoxitin, Cefotetan, Cefmetazole, Carbacephem, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Oxacephem, Cefepime, Cefozopran, Cefpirome, Cefquinome, Ceftobiprole, Ceftiofur, Cefquinome, Cefovecin, CXA-101, Ceftaroline, Ceftobiprole etc.

Typical, non-limiting examples of Lincosamide antibacterial agents include Clindamycin, Lincomycin and the like.

Typical, non-limiting examples of Macrolide antibacterial agents include Azithromycin, Clarithromycin, Dirithromycin, Erythromycin, Roxithromycin, Troleandomycin, Telithromycin, Spectinomycin, Solithromycin and the like.

Typical, non-limiting examples of Monobactam antibacterial agents include Aztreonam and the like.

Typical, non-limiting examples of Nitrofuran antibacterial agents include Furazolidone, Nitrofurantoin and the like.

Typical, non-limiting examples of Penicillin antibacterial agents include Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin and the like.

Typical, non-limiting examples of Polypeptide antibacterial agents include Bacitracin, Colistin, Polymyxin B and the like.

Typical, non-limiting examples of Quinolone antibacterial agents include Ciprofloxacin, Enoxacin, Gatifloxacin, Levofloxacin, Lomefloxacin, Moxifloxacin, Nalidixic acid, Levonadifloxacin, Norfloxacin, Ofloxacin, Trovafloxacin, Grepafloxacin, Sparfloxacin, Temafloxacin and the like.

Typical, non-limiting examples of Sulfonamide antibacterial agents include Mafenide, Sulfonamidochrysoidine, Sulfacetamide, Sulfadiazine, Sulfamethizole, Sulfamethoxazole, Sulfasalazine, Sulfisoxazole, Trimethoprim and the like.

Typical, non-limiting examples of Tetracycline antibacterial agents include Demeclocycline, Doxycycline, Minocycline, Oxytetracycline, Tetracycline, Tigecycline and the like.

Typical, non-limiting examples of Oxazolidinone antibacterial agents include Tedizolid, Linezolid, Ranbezolid, Torezolid, Radezolid etc.

The pharmaceutical compositions according to the invention may include one or more pharmaceutically acceptable carriers or excipients or the like, Typical, non-limiting examples of such carriers or excipient include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, stabilizing agents, binding agents etc.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered to a subject. In some other embodiments, the active ingredients are administered separately. Since the invention contemplates that the active ingredients agents may be administered separately, the invention further provides for combining separate pharmaceutical compositions in kit form. The kit may comprise one or more separate pharmaceutical compositions, each comprising one or more active ingredients. Each of such separate compositions may be present in a separate container such as a bottle, vial, syringes, boxes, bags, and the like. Typically, the kit comprises directions for the administration of the separate components. The kit form is particularly advantageous when the separate components are preferably administered in different dosage forms (e.g., oral and parenteral) ore are administered at different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compounds, compositions and methods according to the invention are also effective in preventing or treating bacterial infections that are caused by bacteria producing one or more beta-lactamase enzymes. The ability of compositions and methods according to the present invention to treat such resistant bacteria with typical beta-lactam antibiotics represents a significant improvement in the art.

In general, the compounds of Formula (I) or a stereoisomer or pharmaceutically acceptable salt thereof according to invention are also useful in increasing antibacterial effectiveness of a antibacterial agent in a subject. The antibacterial effectiveness of one or more antibacterial agents may increased, for example, by co-administering said antibacterial agent or a pharmaceutically acceptable derivative thereof with a pharmaceutically effective amount of a compound of Formula (I) or a stereoisomer or a pharmaceutically acceptable salt thereof according to the invention.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example-1 trans-sulfuric acid mono-[2-(N'—[(S)-pyrrolidin-2-carbonyl]-hydrazinocarbonyl)-7-oxo-1,6-diaza-bicyclo[3.2.1]oct-6-yl]ester

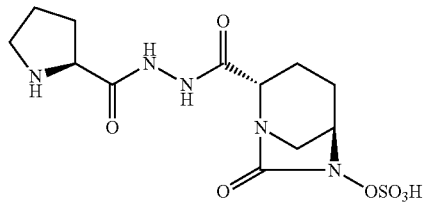

Step-1: Preparation of trans-2-[N'-(6-benzyloxy-7-oxo-1,6-diaza-bicyclo[3.2.1]octane-2-carbonyl)-hydrazinocarbonyl]-(S)-pyrrolidin-1-carboxylic acid tert-butyl ester To a clear solution of trans-6-benzyloxy-7-oxo-1,6-diaza-bicyclo[3.2.1]octane-2-carboxylic acid (15 gm, 0.054 mol) in N,N-dimethyl formamide (150 ml), was added EDC hydrochloride (15.57 gm, 0.082 mol) followed by HOBt (11.0 gm, 0.082 mol) at about 25° C. to 35° C. under stirring. The reaction mixture was stirred for 15 minutes and a solution of (S)-N-tert-butoxycarbonyl-pyrrolidin-2-carboxylic acid hydrazide (14.93 gm, 0.065 mol) dissolved in N,N-dimethyl formamide (75 ml), followed by N,N-di-isopropyl ethylamine (28.4 ml, 0.163 mol) were added. The reaction mixture was stirred at a temperature between 25° C. to 35° C. for 16 hours. The reaction mixture was poured under stirring into 10% aqueous citric acid solution (2250 ml). The resulting mixture was extracted with diethyl ether (1000 ml×3). Combined organic layer was washed with water (1000 ml) followed by brine solution (500 ml) and dried over sodium sulfate. Concentration of organic layer under vacuum afforded the crude residue in 13 gm quantity. The residue was purified using silica gel column chromatography to provide the product (trans-2-[N'-(6-benzyloxy-7-oxo-1,6-diaza-bicyclo[3.2.1]octane-2-carbonyl)-hydrazinocarbonyl]-(S)-pyrrolidin-1-carboxylic acid tert-butyl ester) in 6.3 gm quantity as a white powder.

Analysis: MS (ES+) $C_{24}H_{33}N_5O_6$=488.1 (M+1);

$H^1$NMR (DMSO-$d_6$)=9.86 (br d, 1H), 9.75 (br d, 1H), 7.34-7.44 (m, 5H), 4.92 (dd, 2H), 4.07-4.10 (m, 1H), 3.78-3.82 (m, 1H), 3.68 (br d, 1H), 3.20-3.25 (m, 3H), 2.87 (br d, 1H), 1.62-2.10 (m, 8H), 1.34 (s, 9H).

Step-2: Preparation of trans-2-[N'-(6-hydroxy-7-oxo-1,6-diaza-bicyclo[3.2.1]octane-2-carbonyl)-hydrazinocarbonyl]-(S)-pyrrolidin-1-carboxylic acid tert-butyl ester To a clear solution of step-1 product (3.0 gm, 6.15 mmol) in methanol (30 ml) was added 10% palladium on carbon (300 mg). The suspension was stirred under atmospheric hydrogen pressure at a temperature of about 30° C. for 2 hours. The catalyst was filtered over a celite bed and catalyst-containing bed was washed with additional methanol (10 ml) and dichloromethane (10 ml). The filtrate was concentrated in vacuum to provide a white powder, which was triturated with diethyl ether to provide trans-2-[N'-(6-hydroxy-7-oxo-1,6-diaza-bicyclo[3.2.1]octane-2-carbonyl)-hydrazinocarbonyl]-(S)-pyrrolidin-1-carboxylic acid tert-butyl ester as a white powder in 2.00 gm quantity in 82% yield.

Analysis: MS (ES+) $C_{17}H_{27}N_5O_6$=398.0 (M+1);

$H^1$NMR (DMSO-$d_6$)=9.82 (d, 1H), 9.70-9.80 (m, 2H), 4.08-4.15 (m, 1H), 3.4.0-3.78 (m, 1H), 3.59 (br s, 1H), 3.17-3.40 (m, 3H), 2.97 (br d, 1H), 1.55-2.15 (m, 8H), 1.35 (s, 9H).

Step-3: Preparation of tetrabutylammonium salt of trans-2-[N'-(6-sulfooxy-7-oxo-1,6-diaza-bicyclo[3.2.1]octane-2-carbonyl)-hydrazinocarbonyl]-(S)-pyrrolidin-1-carboxylic acid tetr-butyl ester The product obtained in step-2 (2.00 gm, 5.03 mmol) was dissolved in pyridine (40 ml) and to the clear solution was added pyridine sulfur trioxide complex (4.03 gm, 25.18 mmol). The suspension was stirred at a temperature 25° C. to 35° C. for overnight. The suspension was filtered and the solids were washed with dichloromethane (25 ml×2). The filtrate was evaporated under vacuum and the residue was stirred in 0.5 N aqueous potassium dihydrogen phosphate solution (200 ml) for 0.5 hour. The solution was washed with ethyl acetate (100 ml×4) and layers were separated. To the aqueous layer was added tetrabutylammonium sulphate (1.71 gm, 5.03 mmol) and stirred for four hours at about 25° C. The mixture was extracted with dichloromethane (100 ml×2). The combined organic extract was washed with brine (50 ml) and dried on sodium sulfate and evaporated under vacuum to provide solid, that was triturated with diethyl ether and filtered to provide white powder as a step-3 product (tetrabutylammonium salt of trans-2-[N'-(6-sulfooxy-7-oxo-1,6-diaza-bicyclo[3.2.1]octane-2-carbonyl)-hydrazinocarbonyl]-(S)-pyrrolidin-1-carboxylic acid tetr-butyl ester), in 3.0 gm quantity (83% yield).

Analysis: MS (ES−) $C_{17}H_{26}N_5O_9S.N(C_4H_9)_4$ as a salt=476.0 (M−1) as a free sulfonic acid;

$H^1$NMR (CDCl$_3$)=9.13 (br s, 1H), 8.49 (br s, 1H), 4.35 (br s, 2H), 3.98 (d, 1H), 3.24-3.50 (m, 10H), 3.13 (br d, 1H), 2.35 (dd, 2H), 2.16 (br s, 2H), 1.91-2.01 (m, 4H), 1.61-1.70 (m, 10H), 1.40-1.48 (m, 17H), 0.98-1.02 (m, 12H).

Step-4: trans-sulfuric acid mono-[2-(N'—[(S)-pyrrolidin-2-carbonyl]-hydrazinocarbonyl)-7-oxo-1,6-diaza-bicyclo[3.2.1]oct-6-yl]ester To the powder obtained in step-3 (3.0 gm, 4.17 mmol) was added, a solution of trifluoroacetic acid (7 ml) in dichloromethane (7 ml) slowly by syringe at −5° C. over a period of 5 minutes. The mixture was maintained under stirring for 1 hr. Solvents were removed below 40° C. under high vacuum to provide a residue, which was triturated with diethyl ether (50 ml×5) and each time diethyl ether was decanted. The obtained white solid was further triturated with acetonitrile (100 ml×2). The resultant solid was stirred in dichloromethane (100 ml) and the suspension was filtered. The solid was dried under vacuum to provide title compound of the invention (trans-sulfuric acid mono-[2-(N'—[(S)-pyrrolidin-2-carbonyl]-hydrazinocarbonyl)-7-oxo-1,6-diaza-bicyclo[3.2.1]oct-6-yl]ester) in 1.2 gm quantity (59% yield).

Analysis: MS (ES−) $C_{12}H_{19}N_5O_7S$=376.2 (M−1) as a free sulfonic acid;

$H^1$NMR (DMSO-$d_6$)=10.39 (br s, 1H), 10.15 (s, 1H), 8.96 (br s, 2H), 4.19 (t, 1H), 4.03 (br s, 1H), 3.86 (d, 1H), 3.16-3.25 (m, 3H), 3.02 (br d, 1H), 2.27-2.33 (m, 1H), 1.92-2.23 (m, 1H), 1.84-1.90 (m, 4H), 1.69-1.75 (m, 1H), 1.54-1.62 (m, 1H).

Example-2 trans-sulfuric acid mono-[2-(N'—[(R)-piperidin-3-carbonyl]-hydrazinocarbonyl)-7-oxo-1,6-diaza-bicyclo[3.2.1]oct-6-yl]ester

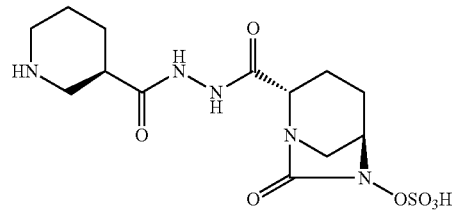

Step-1: Preparation of trans-3-[N'-(6-benzyloxy-7-oxo-1,6-diaza-bicyclo[3.2.1]octane-2-carbonyl)-hydrazinocarbonyl]-(R)-piperidin-1-carboxylic acid tert-butyl ester By using the procedure described in Step-1 of Example-1 above, and by using trans-6-benzyloxy-7-oxo-1,6-diaza-bicyclo[3.2.1]octane-2-carboxylic acid (25 gm, 0.084 mol), N,N-dimethyl formamide (625 ml), EDC hydrochloride (24 gm, 0.126 mol), HOBt (16.96 gm, 0.126 mol), (R)—N-tert-butoxycarbonyl-piperidin-3-carboxylic acid hydrazide (21.40 gm, 0.088 mol) to provide the title compound in 17.0 gm quantity, 41% yield as a white solid.

Analysis: MS (ES+) $C_{25}H_{35}N_5O_6$=502.1 (M+1);

$H^1$NMR (CDCl$_3$)=8.40 (br s, 1H), 7.34-7.44 (m, 5H), 5.05 (d, 1H), 4.90 (d, 1H), 4.00 (br d, 1H), 3.82 (br s, 1H), 3.30 (br s, 1H), 3.16-3.21 (m, 1H), 3.06 (br d, 1H), 2.42 (br s, 1H), 2.29-2.34 (m, 1H), 1.18-2.02 (m, 4H), 1.60-1.75 (m, 4H), 1.45-1.55 (m, 2H), 1.44 (s, 9H).

Step-2: Preparation of trans-3-[N'-(6-hydroxy-7-oxo-1,6-diaza-bicyclo[3.2.1]octane-2-carbonyl)-hydrazinocarbonyl]-(R)-piperidin-1-carboxylic acid tert-butyl ester By using the procedure described in Step-2 of Example-1 above, and by using trans-3-[N'-(6-benzyloxy-7-oxo-1,6-diaza-bicyclo[3.2.1]octane-2-carbonyl)-hydrazinocarbonyl]-(R)-piperidin-1-carboxylic acid tert-butyl ester (16.5 gm, 0.033 mol), methanol (170 ml) and 10% palladium on carbon (3.5 gm) to provide the title compound in 13.5 gm quantity as a pale pink solid and it was used for the next reaction immediately.

Analysis: MS (ES+) $C_{18}H_{29}N_5O_6$=411.1 (M+1);

Step-3: Preparation of tetrabutylammonium salt of trans-3-[N'-(6-sulfooxy-7-oxo-1,6-diaza-bicyclo[3.2.1]octane-2-carbonyl)-hydrazinocarbonyl]-(R)-piperidin-1-carboxylic acid tert-butyl ester By using the procedure described in Step-3 of Example-1 above, and by using trans-3-[N'-(6-hydroxy-7-oxo-1,6-diaza-bicyclo[3.2.1]octane-2-carbonyl)-hydrazinocarbonyl]-(R)-piperidin-1-carboxylic acid tert-butyl ester (13.5 gm, 0.033 mol), pyridine (70 ml) and pyridine sulfur trioxide complex (26.11 gm, 0.164 mol), 0.5 N aqueous potassium dihydrogen phosphate solution (400 ml) and tetrabutylammonium sulphate (9.74 gm, 0.033 mol) to provide the title compound in 25 gm quantity as a yellowish solid, in quantitative yield.

Analysis: MS (ES−) $C_{18}H_{28}N_5O_9S.N(C_4H_9)_4$ as a salt=490.0 (M−1) as a free sulfonic acid;

Step-4: trans-sulfuric acid mono-[2-(N'—[(R)-piperidin-3-carbonyl]-hydrazinocarbonyl)-7-oxo-1,6-diaza-bicyclo[3.2.1]oct-6-yl]ester By using the procedure described in Step-4 of Example-1 above, and by using tetrabutylammonium salt of trans-3-[N'-(6-sulfooxy-7-oxo-1,6-diaza-bicyclo[3.2.1]octane-2-carbonyl)-hydrazinocarbonyl]-(R)-piperidin-1-carboxylic acid tert-butyl ester (24 gm, 0.032 mmol), dichloromethane (60 ml) and trifluoroacetic acid (60 ml) to provide the title compound in 10 gm quantity as a white solid, in 79% yield.

Analysis: MS (ES−)=$C_{13}H_{21}N_5O_7S$=390.2 (M−1) as a free sulfonic acid;

$H^1$NMR (DMSO-$d_6$)=9.97 (d, 2H), 8.32 (br s, 2H), 4.00 (br s, 1H), 3.81 (d, 1H), 3.10-3.22 (m, 3H), 2.97-3.02 (m, 2H), 2.86-2.91 (m, 1H), 2.65-2.66 (m, 1H), 1.97-2.03 (m, 1H), 1.57-1.88 (m, 7H).

$[α]_D^{25}$=−32.6°, (c 0.5, water).

Example-3 trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester

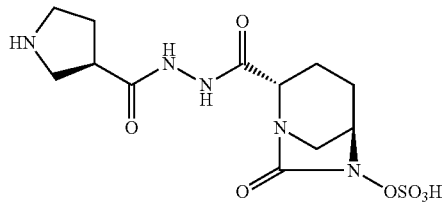

Step-1: Preparation of trans-3-[N'-(6-benzyloxy-7-oxo-1,6-diaza-bicyclo[3.2.1]octane-2-carbonyl)-hydrazinocarbonyl]-(R)-pyrrolidin-1-carboxylic acid tert-butyl ester By using the procedure described in Step-1 of Example-1, and by using trans-6-benzyloxy-7-oxo-1,6-diaza-bicyclo[3.2.1]octane-2-carboxylic acid (15.7 gm, 0.057 mol), N,N-dimethyl formamide (390 ml), EDC hydrochloride (16.24 gm, 0.085 mol), HOBt (11.48 gm, 0.085 mol), (R)-N-tert-butoxycarbonyl-pyrrolidin-3-carboxylic acid hydrazide (13.7 gm, 0.06 mol) to provide the title compound in 11.94 gm quantity, 43% yield as a white solid.

Analysis: MS (ES+) $C_{24}H_{33}N_5O_6$=488.2 (M+1);

$H^1$NMR (CDCl$_3$), D$_2$O exchange=7.30-7.39 (m, 5H), 4.85 (s, 2H), 3.77 (d, 1H), 3.68 (br s, 1H), 3.39-3.41 (m, 1H), 3.17-3.26 (m, 3H), 3.01 (d, 1H), 2.90-2.92 (m, 2H), 1.97-2.03 (m, 2H), 1.79-1.89 (m, 2H), 1.66-1.70 (m, 1H), 1.55-1.57 (m, 1H), 1.32 (s, 9H).

Step-2: Preparation of trans-3-[N'-(6-hydroxy-7-oxo-1,6-diaza-bicyclo[3.2.1]octane-2-carbonyl)-hydrazinocarbonyl]-(R)-pyrrolidin-1-carboxylic acid tert-butyl ester By using the procedure described in Step-2 of Example-1, and by using trans-3-[N'-(6-benzyloxy-7-oxo-1,6-diaza-bicyclo[3.2.1]octane-2-carbonyl)-hydrazinocarbonyl]-(R)-pyrrolidin-1-carboxylic acid tert-butyl ester (11.5 gm, 0.024 mol), methanol (115 ml) and 10% palladium on carbon (3.0 gm) to provide the title compound in 9.5 gm quantity as a pale brown solid and it was used for the next reaction immediately.

Analysis: MS (ES+) $C_{17}H_{27}N_5O_6$=398.2 (M+1);

Step-3: Preparation of tetrabutylammonium salt of trans-3-[N'-(6-sulfooxy-7-oxo-1,6-diaza-bicyclo[3.2.1]octane-2-carbonyl)-hydrazinocarbonyl]-(R)-pyrrolidin-1-carboxylic acid tert-butyl ester By using the procedure described in Step-3 of Example-1, and by using trans-3-[N'-(6-hydroxy-7-oxo-1,6-diaza-bicyclo[3.2.1]octane-2-carbonyl)-hydrazinocarbonyl]-(R)-pyrrolidin-1-carboxylic acid tert-butyl ester (9.5 gm, 0.024 mol), pyridine (95 ml) and pyridine sulfur trioxide complex (19.08 gm, 0.12 mol), 0.5 N aqueous potassium dihydrogen phosphate solution (300 ml) and tetrabutylammonium sulphate (8.15 gm, 0.024 mol) to provide the title compound in 15.3 gm quantity as a yellowish solid, in 87% yield.

Analysis: MS (ES−) $C_{17}H_{26}N_5O_9S.N(C_4H_9)_4$ as a salt=476.1 (M−1) as a free sulfonic acid;

$H^1$NMR (DMSO-$d_6$)=9.82 (d, 2H), 3.97 (br s, 1H), 3.79 (d, 1H), 3.42-3.44 (m, 1H), 3.00-3.18 (m, 10H), 2.65-2.97 (m, 2H), 1.98-2.01 (m, 2H), 1.74-1.83 (m, 2H), 1.63-1.72 (m, 1H), 1.38-1.55 (m, 9H), 1.33 (s, 9H), 1.24-1.28 (m. 8H), 0.91-0.99 (m, 12H).

Step-4: trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester By using the procedure described in Step-4 of Example-1, and by using tetrabutylammonium salt of trans-3-[N'-(6-sulfooxy-7-oxo-1,6-diaza-bicyclo[3.2.1]octane-2-carbonyl)-hydrazinocarbonyl]-(R)-pyrrolidin-1-carboxylic acid tert-butyl ester (15 gm, 0.021 mmol), dichloromethane (37 ml) and trifluoroacetic acid (37 ml) to provide the title compound in 7.7 gm quantity as a white solid.

Analysis: MS (ES−)=$C_{12}H_{19}N_5O_7S$=376.1 (M−1) as a free sulfonic acid;

$H^1$NMR (DMSO-$d_6$)=10.04 (s, 1H), 9.96 (s, 1H), 8.79 (br s, 1H), 8.68 (br s, 1H), 4.00 (br s, 1H), 3.82 (d, 1H), 3.18-3.32 (m, 4H), 3.08-3.12 (m, 1H), 3.00 (br d, 1H), 2.05-2.29 (m, 1H), 1.96-2.05 (m, 2H), 1.84-1.87 (m, 1H), 1.69-1.73 (m, 1H), 1.56-1.67 (m, 1H). $[α]_D^{25}$−44.2°, (c 0.5, water).

Example-4 trans-{7-oxo-2-[N'—((R)-piperidin-3-carbonyl)-hydrazinocarbonyl]-1,6-diaza-bicyclo[3.2.1]-oct-6-yloxy}-acetic acid

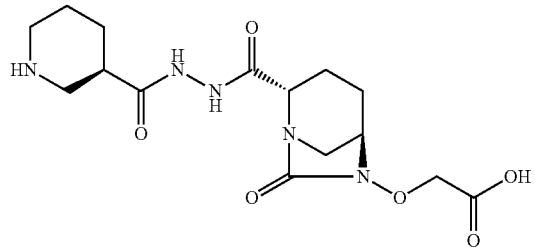 [SMILES: O=C(O)CON1C(=O)N2C[C@H]1CC[C@H]2C(=O)NNC(=O)[C@@H]1CCCNC1]

Step-1: Preparation of trans-3-{N'-(6-ethoxycarbonylmethoxy-7-oxo-1,6-diaza-bicyclo[3.2.1]octane-2-carbonyl)-hydrazinocarbonyl}-(R)-piperidin-1-carboxylic acid tert-butyl ester The intermediate compound trans-3-[N'-(6-hydroxy-7-oxo-1,6-diaza-bicyclo[3.2.1]octane-2-carbonyl)-hydrazinocarbonyl]-(R)-piperidin-1-carboxylic acid tert-butyl ester (4.0 gm, 9.73 mmol), obtained in Step-2 of Example-2) was dissolved in DMF (12 ml) and to the clear solution was added potassium carbonate (1.61 gm, 11.6 mmol) followed by ethyl bromo acetate (1.2 ml, 10.0 mmol) under stirring and the suspension was stirred for 18 hours at about 25° C. The reaction was monitored by TLC. DMF was evaporated under vacuum to provide a residue. The residue was purified by silica gel column chromatography to provide titled Step-1 intermediate compound in 2.6 gm quantity as a solid in 53.7% yield.

Analysis: MS(+)=$C_{22}H_{35}N_5O_8$=498.1 (M+1);

$H^1$NMR (CDCl$_3$)=8.45 (br s, 2H), 4.58 (s, 2H), 4.19-4.27 (m, 2H), 4.02-4.12 (m, 2H), 3.25 (br d, 1H), 3.15 (br d, 1H), 2.38 (br s, 1H), 2.35 (dd, 1H), 2.15-2.20 (m, 1H), 1.79-2.02 (m, 4H), 1.67-1.77 (m, 4H), 1.44-1.51 (m, 11H), 1.28 (t, 3H).

Step-2: Preparation of trans-3-{N'-(6-carboxymethoxy-7-oxo-1,6-diaza-bicyclo[3.2.1]octane-2-carbonyl)-hydrazinocarbonyl}-(R)-piperidin-1-carboxylic acid tert-butyl ester To a clear solution of trans-3-{N'-(6-ethoxycarbonyl-methoxy-7-oxo-1,6-diaza-bicyclo[3.2.1]octane-2-carbonyl)-hydrazinocarbonyl}-(R)-piperidin-1-carboxylic acid tert-butyl ester (600 mg, 1.20 mmol) in tetrahydrofuran (32 ml) and water (12 ml) was added lithium hydroxide (43.2 mg, 1.8 mmol) at 0° C. The reaction mixture was stirred for 3 hours and was neutralized to pH 6 by addition of aqueous 1 N potassium hydrogen sulfate. It was exacted with ethyl acetate (3×25 ml). Layers were separated and aqueous layer was acidified with 1 N potassium hydrogen sulfate to pH 1 and extracted with ethyl acetate (3×25 ml). The Organic layer was dried over sodium sulfate and evaporated to dryness under vacuum to provide 160 mg of tilted intermediate as a solid in 27% yield.

Analysis: MS (ES+)=$C_{20}H_{31}N_5O_8$=470.1 (M+1)

$H^1$NMR (CDCl$_3$)=8.40 (br s, 2H), 4.67 (d, 1H), 4.52 (d, 1H), 4.07-4.14 (m, 2H), 3.95 (br s, 1H), 3.43 (br d, 1H), 3.19 (br d, 1H), 2.47 (br s, 1H), 2.39 (dd, 1H), 2.09-2.13 (m, 2H), 1.77-2.00 (m, 4H), 1.68-1.77 (m, 2H), 1.45-1.51 (m, 11H).

Step-3: trans-{7-oxo-2-[N'—((R)-piperidin-3-carbonyl)-hydrazinocarbonyl]-1,6-diaza-bicyclo[3.2.1]-oct-6-yloxy}-acetic acid To a clear solution of trans-3-{N'-(6-carboxymethoxy-7-oxo-1,6-diaza-bicyclo[3.2.1]octane-2-carbonyl)-hydrazinocarbonyl}-(R)-piperidin-1-carboxylic acid tert-butyl ester (150 mg, 0.32 mmol) in dichloromethane (2 ml) was added trifluoroacetic acid under stirring at −10° C. The reaction mixture was stirred for about 1 hour at −10° C. and the solvents were evaporated under vacuum to provide a residue. The residue was triturated successively with diethyl ether (25 ml) and acetonitrile (25 ml) and solvents were decanted to provide solid that was dried under vacuum to provide 59 mg of titled compound in 50% yield.

Analysis: MS (ES−)=$C_{15}H_{23}N_5O_6$=368.0 (M−1)

$H^1$NMR (DMSO-d$_6$)=9.97 (br s, 2H), 4.48 (d, 1H), 4.29 (d, 1H), 3.91 (s, 1H), 3.83 (d, 1H), 3.36 (q, 1H), 3.11-3.21 (m, 4H), 2.84-3.01 (m, 3H), 2.66 (br s, 1H), 1.90-2.05 (m, 3H), 1.69-1.76 (m, 2H), 1.59-1.66 (m, 3H).

Example-5 trans-difluoro-{7-oxo-2-[N'—((R)-piperidin-3-carbonyl)-hydrazinocarbonyl]-1,6-diaza-bicyclo[3.2.1]-oct-6-yloxy}-acetic acid

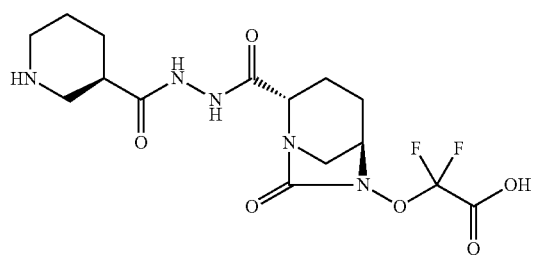 [SMILES: O=C(NNC(=O)[C@@H]1CC[C@@H]2CN1C(=O)N2OC(F)(F)C(=O)O)[C@@H]1CCCNC1]

By using procedure the described in Example 4 and by using ethyl-bromo difluoroacetate (2.0 gm, 10.0 mmol) in the place of ethyl bromo acetate, the titled compound was prepared in 30 mg quantity as a solid.

Analysis: MS (ES+)=$C_{15}H_{21}F_2N_5O_6$=406.2 (M+1)

$H^1$NMR (DMSO-d$_6$)=10.99 (d, 2H), 8.59 (br s, 2H), 3.89-4.00 (m, 2H), 3.13-3.31 (m, 4H), 2.95-3.07 (m, 2H), 2.81-2.88 (m, 1H), 2.62-2.78 (m, 1H), 1.97-2.05 (m, 1H), 1-84-1.95 (m, 1H), 1.72-1.79 (m, 2H), 1.59-1.64 (m, 3H).

Compounds 6 to 42 (Table 1) were prepared using the procedure described as in Example-1 and using corresponding $R_1$CONHNH$_2$, in place of (S)—N-tert-butoxycarbonyl-pyrrolidin-2-carboxylic acid hydrazide.

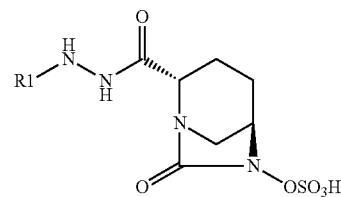

TABLE 1

| Example No. | Acid hydrazide ($R_1$CONHNH$_2$) | $R_1$ | $H^1$ NMR (DMSO-d$_6$) | Mass (ES-1) as free acid (MF) |
|---|---|---|---|---|
| 6. | t-Boc-NHNH$_2$ | H | 11.05 (br s, 1H), 9.39 (br s, 2H), 4.04 (d, 1H), 3.92 (d, 1H), 3.04 (br d, 1H), 2.48 (d, 1H), 1.99-2.05 (m, 1H), 1.86-1.90 (m, 1H), 1.63-1.77 (m, 2H). | 279.1 ($C_7H_{12}N_4O_6S$) |
| 7. | t-Boc-HNCH$_2$—CO NHNH$_2$ | H$_2$NCH$_2$—CO— | 10.20 (bs, 1H), 8.20 (br s, 3H), 4.01 (br s, 1H), 3.86 (br d, 1H), 3.61 (s, 2H), 2.99 (d, 1H), 1.97-2.05 (m, 1H), 1.78-1.88 (m, 1H), 1.68-1.72 (m, 1H), 1.54-1.67 (m, 2H). | 336.2 ($C_9H_{15}N_5O_7S$) |
| 8. | t-Boc-HNCH$_2$CH$_2$—CONHNH$_2$ | H$_2$NCH$_2$CH$_2$—CO— | 9.34 (d, 2H), 7.66 (br s, 2H), 4.00 (br d, 1H), 3.84 (d, 1H), 3.16 (d, 1H), 2.92-3.00 (m, 3H), 2.43-2.53 (m, 2H), 1.85- | 350.2 ($C_{10}H_{16}N_5O_7S$) |

TABLE 1-continued

| Example No. | Acid hydrazide (R₁CONHNH₂) | R₁ | H¹ NMR (DMSO-d₆) | Mass (ES-1) as free acid (MF) |
|---|---|---|---|---|
| 9. | t-Boc-HN—(CH₂)₃—CONHNH₂ | H₂N(CH₂)₃—CO— | 2.05 (m, 1H), 1.74-1.75 (m, 1H), 1.51-1.73 (m, 2H). 9.87 (s, 1H), 9.77 (s, 1H), 7.63 (br s, 3H), 4.00 (br s, 1H), 3.86 (d, 1H), 3.16 (d, 1H), 2.76-2.73 (m, 2H), 2.20 (t, 2H), 1.97-2.01 (m, 1H), 1.51-1.84 (m, 6H). | 363.9 ($C_{11}H_{19}N_5O_7S$) |
| 10. | [2,2-dimethyloxazolidine-4-carbohydrazide structure] | [HO-CH₂-CH(NH₂)-CO- structure] | 10.33 (s, 1H), 10.09 (s, 1H), 8.19 (br s, 3H), 5.48 (br s, 1H), 4.02 (br s, 1H), 3.86 (d, 1H), 3.79 (d, 1H), 3.64-3.68 (m, 1H), 3.21 (d, 1H), 3.02 (d, 1H), 1.98-2.05 (m, 1H), 1.82-1.88 (m, 1H), 1.68-1.75 (m, 1H), 1.54-1.62 (m, 1H). | 366.2 ($C_{10}H_{17}N_5O_8S$) |
| 11. | [4-fluoro-N-boc-pyrrolidine-2-carbohydrazide structure] | [4-fluoropyrrolidine-2-carbonyl structure] | 10.46 (s, 1H), 10.20 (s, 1H), 9.73 (br s, 1H), 9.15 (br s, 1H), 5.44 (br s, 1H), 5.31-4.45 (m, 1H), 3.99 (br s, 1H), 3.87 (d, 1H), 3.61 (dd, 2H), 3.28-3.42 (m, 1H), 3.02-3.12 (m, 2H), 2.60-2.82 (m, 1H), 2.30-2.42 (m, 1H), 1.99-2.04 (m, 1H), 1.80-1.90 (m, 1H), 1.58-1.74 (m, 2H). | 393.9 ($C_{12}H_{18}N_5FO_7S$) |
| 12. | [4-methoxy-N-boc-pyrrolidine-2-carbohydrazide structure] | [4-methoxypyrrolidine-2-carbonyl structure] | 10.41 (s, 1H), 10.19 (s, 1H), 9.59 (br s, 1H), 8.97 (br s, 1H), 4.19-4.24 (m, 1H), 4.13 (br s, 1H), 4.02 (br s, 1H), 3.87 (d, 1H), 3.38 (s, 3H), 3.16-3.33 (m, 3H), 3.02 (br d, 1H), 1.57-2.05 (m, 6H). | 406.2 ($C_{13}H_{21}N_5O_8S$) |
| 13. | [N-Boc-piperidine-4-carbohydrazide structure] | [piperidine-4-carbonyl structure] | 9.82 (d, 1H), 8.41 (br d, 1H), 8.19 (br d, 1H), 3.99 (br s, 1H), 3.80 (d, 1H), 3.18-3.39 (m, 5H), 2.90-3.00 (m, 3H), 1.97-2.03 (m, 1H), 1.75-1.84 (m, 2H), 1.67-1.71 (m, 3H), 1.57-1.62 (m, 2H). | 390.3 ($C_{13}H_{21}N_5O_7S$) |
| 14. | [N-Boc-piperidine-3-carbohydrazide (racemic) structure] | [piperidine-3-carbonyl structure] | 9.99 (d, 2H), 8.40 (br s, 2H), 4.00 (br s, 1H), 3.81 (d, 1H), 3.10-3.21 (m, 4H), 2.91-3.01 (m, 3H), 2.65-2.66 (m, 1H), 1.97-2.05 (m, 1H), 1.54-1.88 (m, 7H). | 389.9 ($C_{13}H_{21}N_5O_7S$) |
| 15. | [N-Boc-(3S)-piperidine-3-carbohydrazide structure] | [(3S)-piperidine-3-carbonyl structure] | 9.96 (d, 2H), 8.39 (br s, 2H), 4.00 (br s, 1H), 3.81 (d, 1H), 3.09-3.17 (m, 3H), 2.97-3.02 (m, 1H), 2.87-2.92 (m, 1H), 2.60-2.65 (m, 1H), 1.97-2.02 (m, 1H), 1.58-1.84 (m, 8H). | 390.2 ($C_{13}H_{21}N_5O_7S$) |
| 16. | [N-boc-piperidine-2-carbohydrazide structure] | [piperidine-2-carbonyl structure] | 10.29 (d, 1H), 10.16 (d, 1H), 8.90-9.03 (m, 1H), 8.70-8.78 (m, 1H), 4.02 (br s, 1H), 3.82-3.87 (m, 2H), 3.12-3.22 (m, 2H), 2.93-3.03 (m, 2H), 1.86-2.10 (m, 2H), 1.24-1.72 (m, 8H). | 390.2 ($C_{13}H_{21}N_5O_7S$) |

TABLE 1-continued

| Example No. | Acid hydrazide (R₁CONHNH₂) | R₁ | H¹ NMR (DMSO-d₆) | Mass (ES-1) as free acid (MF) |
|---|---|---|---|---|
| 17. | (piperidine-2-carbohydrazide, N-Boc) | (piperidine-2-carbonyl, NH) | 10.30 (s, 1H), 10.14 (s, 1H), 9.00 (br d, 1H), 8.70-8.75 (m, 1H), 4.02 (br s, 1H), 3.81-3.87 (m, 2H), 3.17-3.21 (m, 2H), 2.93-3.03 (m, 2H), 2.10 (br d, 1H), 1.98-2.05 (m, 1H), 1.85-1.92 (m, 1H), 1.69-1.77 (m, 3H), 1.46-1.66 (m, 4H). | 390.3 (C₁₃H₂₁N₅O₇S) |
| 18. | (piperidine-2-carbohydrazide, N-Boc, other stereo) | (piperidine-2-carbonyl, NH) | 10.27 (s, 1H), 10.17 (s, 1H), 8.93 (br d, 1H), 8.76-8.78 (m, 1H), 4.02 (br s, 1H), 3.79-3.86 (m, 2H), 3.18-3.23 (m, 2H), 2.93-3.02 (m, 2H), 2.14 (br d, 1H), 1.97-2.05 (m, 1H), 1.83-1.93 (m, 1H), 1.46-1.77 (m, 7H). | 390.3 (C₁₃H₂₁N₅O₇S) |
| 19. | (Boc-piperazin-1-yl acetohydrazide) | (piperazin-1-yl acetyl) | 10.00 (d, 1H), 9.68 (br s, 1H), 4.01 (br s, 1H), 3.83 (d, 1H), 3.42 (s, 1H), 3.12-3.21 (m, 6H), 2.93-3.02 (m, 4H), 1.98-2.05 (m, 1H), 1.84-1.92 (m, 1H), 1.68-1.72 (m, 1H), 1.54-1.62 (m, 1H). | 404.9 (C₁₃H₂₂N₆O₇S) |
| 20. | (Boc-NH-CH(Ph)-CONHNH₂) | (H₂N-CH(Ph)-CO-) | 10.44 (d, 1H), 10.18 (d, 1H), 8.67 (br d, 3H), 7.43-7.55 (m, 5H), 4.98 (br s, 1H), 4.01 (s, 1H), 3.83 (br d, 1H), 3.19 (d, 1H), 3.00 (br d, 1H), 1.85-2.05 (m, 2H), 1.59-1.72 (m, 2H). | 411.9 (C₁₅H₁₉N₅O₇S) |
| 21. | (RS)-t-Boc-HNCH(CH₃)—CH₂CONHNH₂ | (RS)—H₂NCH(CH₃)CH₂—CO— | 10.00 (s, 1H), 9.95 (d, 1H), 7.74 (br s, 3H), 4.01 (br s, 1H), 3.83 (d, 1H), 3.53-3.48 (m, 1H), 3.12-3.19 (m, 1H), 3.00 (br d, 1H), 2.36-2.42 (m, 1H), 1.98-2.06 (m, 1H), 1.78-1.87 (m, 1H), 1.66-1.76 (m, 1H), 1.54-1.62 (m, 2H), 1.19 (d, 3H) | 364.1 (C₁₁H₁₉N₅O₇S) |
| 22. | Boc—HN—C(CH₃)₂—CONHNH₂ | H₂N—C(CH₃)₂—CO— | 9.92 (S, 1H), 9.82 (S, 1H), 7.71 (br s, 3H), 4.01 (br s, 1H), 3.84 (d, 1H), 3.21 (d, 1H), 3.01 (br d, 1H), 2.85-2.92 (m, 2H), 1.98-2.04 (m, 1H), 1.85-1.87 (m, 1H), 1.69-1.73 (m, 1H), 1.57-1.60 (m, 1H), 1.22 (d, 6H). | 378.2 (C₁₂H₂₁N₅O₇S) |
| 23. | Boc—HN—CH₂—(cyclopropane)—CONHNH₂ | H₂N—CH₂—(cyclopropane)—CO— | 9.82 (s, 1H), 7.76 (br s, 3H), 4.00 (br s, 1H), 3.81 (d, 1H), 3.22 (d, 1H), 2.00 (d, 2H), 2.88 (d, 1H), 1.97-2.05 (m, 1H), 1.74-1.85 (m, 1H), 1.16-1.73 (m, 1H), 1.54-1.61 (m, 1H), 1.27 (t, 2H) 1.01-1.08 (m, 2H). | 376.2 (C₁₂H₁₉N₅O₇S) |
| 24. | (Boc-Gln-hydrazide) | (Gln-CO-) | 10.37 (s, 1H), 10.16 (s, 1H), 8.24 (br s, 3H), 7.39 (br s, 1H), 6.95 (br s, 1H), 4.02 (br s, 1H), 3.86 (d, 1H), 3.19 (d, 1H), 3.02 (br d, 1H), 2.20-2.34 (m, 2H), 1.92-2.05 (m, 4H), 1.67-1.79 (m, 1H), 1.55-1.63 (m, 1H). | 407.2 (C₁₂H₂₀N₆O₈S) |

TABLE 1-continued

| Example No. | Acid hydrazide (R₁CONHNH₂) | R₁ | H¹ NMR (DMSO-d₆) | Mass (ES-1) as free acid (MF) |
|---|---|---|---|---|
| 25. | t-Boc—HN—(CH₂)₄—CONHNH₂ | H₂N(CH₂)₄—CO— | 9.18 (s, 1H), 9.70 (s, 1H), 7.58 (br s, 3H), 3.99 (br s, 1H), 3.80 (d, 1H), 3.21 (d, 1H), 3.99 (br d, 1H), 2.76-(br s, 2H), 2.15-2.20 (m, 1H), 1.97-2.01 (m, 1H), 1.82-1.85 (m, 1H), 1.67-1.73 (m, 1H), 1.55-1.62 (m, 6H). | 378.2 (C₁₂H₂₁N₅O₇S) |
| 26. | 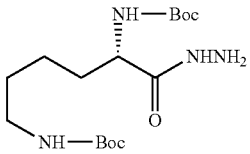 [SMILES: CC(C)(C)OC(=O)NCCCC[C@H](NC(=O)OC(C)(C)C)C(=O)NN] | 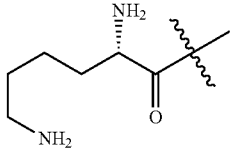 [SMILES: *C(=O)[C@@H](N)CCCCN] | 10.16 (s, 1H), 7.86 (br s, 6H), 4.03 (br s, 1H), 3.88 (d, 1H), 3.77 (t, 1H), 3.16 (d, 1H), 3.02 (br d, 1H), 2.73 (t, 2H), 1.99-2.05 (m, 1H), 1.72-1.76 (m, 1H), 1.62-1.71 (m, 3H), 1.13-1.60(m, 6H). | 407.2 (C₁₃H₂₄N₆O₇S•CF₃COOH) |
| 27. | 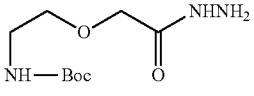 [SMILES: CC(C)(C)OC(=O)NCCOCC(=O)NN] | 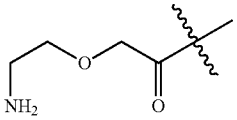 | 9.97 (s, 1H), 9.71 (s, 1H), 7.74 (br s, 3H), 4.04 (s, 2H) 4.01 (br s, 1H), 3.83 (d, 1H), 3.64 (t, 2H), 3.20 (d, 1H) 3.00-3.05 (m, 3H), 1.98-2.05 (m, 1H), 1.82-1.86 (m, 1H), 1.68-1.73 (m, 1H), 1.58-1.63 (m, 1H). | 380.2 (C₁₁H₁₉N₅O₈S) |
| 28. | 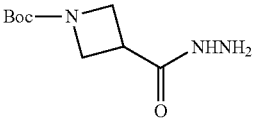 [SMILES: CC(C)(C)OC(=O)N1CC(C(=O)NN)C1] | 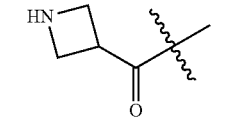 | 10.03 (br s, 1H), 8.66 (br s, 1H), 4.05-4.12 (m, 1H), 3.96-4.01 (m, 4H), 3.84 (d, 1H), 3.53-3.58 (m, 1H), 3.21 (d, 1H), 3.01 (br d, 1H), 1.98-2.03 (m, 1H), 1.72-1.85 (m, 1H), 1.68-1.71 (m, 1H), 1.57-1.62 (m, 1H). | 362.2 (C₁₁H₁₇N₅O₇S) |
| 29. | 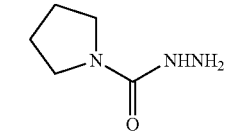 | 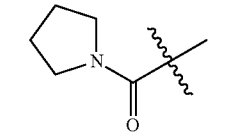 [SMILES: *C(=O)N1CCCC1] | 9.49 (s, 1H), 8.08 (s, 1H), 3.98 (br s, 1H), 3.76 (d, 1H), 3.35 (d, 2H), 3.20-3.25 (m, 4H), 2.96 (br d, 1H), 1.86-2.06 (m, 1H), 1.57-1.80 (m, 7H). | 376.1 (C₁₂H₁₉N₅O₇S) |
| 30. | 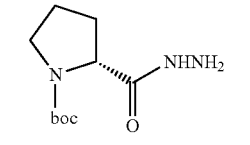 | 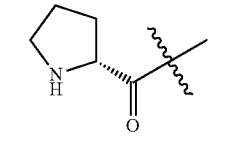 | 10.35 (br s, 1H), 10.18 (s, 1H), 8.96 (br s, 2H), 4.18 (t, 1H), 4.01 (br s, 1H), 3.86 (d, 1H), 3.17-3.25 (m, 3H), 3.01 (br d, 1H), 2.31-2.35 (m, 1H), 1.98-2.03 (m, 1H), 1.76-1.91 (m, 4H), 1.66-1.74 (m, 1H), 1.57-1.62 (m, 1H). | 376.2 (C₁₂H₁₉N₅O₇S) |
| 31. | 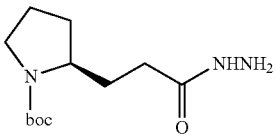 | 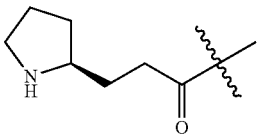 [SMILES: *C(=O)CC[C@@H]1CCCN1] | 9.88 (s, 1H), 9.81 (s, 1H), 8.77 (br s, 1H), 8.29 (br s, 1H), 4.00 (br s, 1H), 3.81 (d, 1H), 3.37-3.43 (m, 1H), 3.12-3.19 (m, 4H), 2.63 (br d, 1H), 2.08-2.24 (m, 2H), 1.69-2.06 (m, 6H), 1.47-1.61 (m, 3H). | 404.2 (C₁₄H₂₃N₅O₇S) |
| 32. | 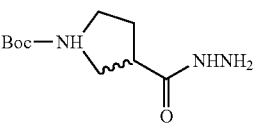 [SMILES: CC(C)(C)OC(=O)N1CCC(C(=O)NN)C1] | 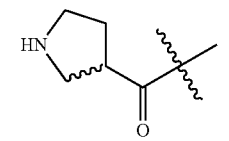 [SMILES: *C(=O)C1CCNC1] | 10.02 (d, 1H), 9.96 (s, 1H), 8.80 (br s, 1H), 8.68 (br s, 1H), 4.00 (br s, 1H), 3.83 (d, 1H), 3.08-3.17 (m, 6H), 3.00 (br d, 1H), 2.06-2.21 (m, 1H), 1.98-2.06 (m, 2H), 1.78-1.82 (m, 1H), 1.67-1.75 (m, 1H), 1.53-1.65 (m, 1H). | 376.2 (C₁₂H₁₉N₅O₇S) |

TABLE 1-continued

| Example No. | Acid hydrazide (R₁CONHNH₂) | R₁ | H¹ NMR (DMSO-d₆) | Mass (ES-1) as free acid (MF) |
|---|---|---|---|---|
| 33. | | | 10.03 (s, 1H), 9.96 (s, 1H), 8.80 (br s, 1H), 8.68 (br s, 1H), 4.00 (br s, 1H), 3.82 (d, 1H), 3.26-3.37 (m, 4H), 3.17-3.25 (m, 1H), 3.06-3.10 (m, 1H), 3.00 (br d, 1H), 2.16-2.23 (m, 1H), 2.00-2.05 (m, 1H), 1.86-1.85 (m, 1H), 1.65-1.75 (m, 1H), 1.53-1.61 (m, 1H). | 376.1 ($C_{12}H_{19}N_5O_7S$) |
| 34. | | | 10.44 (s, 1H), 10.17 (s, 1H), 9.62 (br s, 1H), 8.92 (br s, 1H), 5.48-5.52 (m, 1H), 4.44 (br s, 1H), 4.33 (t, 1H), 4.01 (s, 1H), 3.86 (d, 1H), 3.19 (d, 1H), 3.00-3.10 (m, 2H), 2.26-2.31 (m, 1H), 1.87-2.06 (m, 4H), 1.66-1.75 (m, 1H), 1.54-1.62 (m, 1H). | 392.3 ($C_{12}H_{19}N_5O_8S$) |
| 35. | | | 10.28 (s, 1H), 9.11 (br s, 1H), 8.05 (br s, 2H), 4.29 (t, 1H), 4.03 (br s, 1H), 3.87-3.95 (m, 2H), 3.48-3.53 (m, 2H), 3.04-3.24 (m, 3H), 3.02 (br d, 1H), 2.72-2.79 (m, 1H), 1.99-2.04 (m, 1H), 1.88-1.93 (m, 2H), 1.69-1.78 (m, 1H), 1.54-1.63 (m, 1H). | 391.2 ($C_{10}H_{20}N_6O_7S$) |
| 36. | | | 10.48 (br s, 1H), 10.20 (s, 1H), 7.73 (d, 1H), 7.32 (br s, 4H), 4.16-4.26 (m, 2H), 4.03 (br s, 1H), 3.87 (d, 1H), 3.51-3.56 (m, 1H), 3.01-3.17 (m, 3H), 2.74-2.86 (m, 1H), 1.99-2.05 (m, 1H), 1.55-1.86 (m, 5H). | 433.2 ($C_{13}H_{22}N_8O_7S$) |
| 37. | | | D₂O exchange: 3.98 (br s, 1H), 3.85 (d, 1H) 3.17 (br d, 1H), 3.02-3.11 (m, 2H), 2.92-2.98 (m, 1H), 2.77 (t, 1H), 2.25-2.28 (m, 2H), 2.00-2.04 (m, 1H), 1.75-1.86 (m, 3H), 1.60-1.71 (m, 4H), 1.23-1.47 (m, 4H). | 418.0 ($C_{15}H_{25}N_5O_7S$) |
| 38. | | | 10.54 (br s, 1H), 10.22 (d, 1H), 8.96 (br s, 2H), 4.09 (d, 1H), 4.02 (br s, 1H), 3.87 (d, 1H), 3.62 (t, 2H), 3.38 (t, 3H), 3.01-3.17 (m, 4H), 1.98-2.05 (m, 1H), 1.86-1.88 (m, 1H), 1.68-1.75 (m, 1H), 1.55-1.62 (m, 1H). | 391.3 ($C_{12}H_{20}N_6O_7S \cdot CF_3COOH$) |
| 39. | | | 10.46 (s, 1H), 10.18 (s, 1H), 9.37 (br d, 2H), 4.13 (br d, 2H), 4.02 (br s, 1H), 3.86 (br d, 2H), 3.57-3.62 (m, 2H), 3.17 (br d, 3H), 3.02 (br d, 1H), 1.98-2.04. (m, 1H), 1.85-1.94 (m, 1H), 1.66-1.76 (m, 1H), 1.56-1.61 (m, 1H). | 392.2 ($C_{12}H_{19}N_5O_8S$) |

TABLE 1-continued

| Example No. | Acid hydrazide (R₁CONHNH₂) | R₁ | H¹ NMR (DMSO-d₆) | Mass (ES-1) as free acid (MF) |
|---|---|---|---|---|
| 40. | Boc-N(piperazine)-CO-CH₂-CO-NHNH₂ | HN(piperazine)-CO-CH₂-CO- | $D_2O$ exchange: 3.97 (br s, 1H), 3.83 (d, 1H), 3.59-3.68 (m, 4H), 3.40 (s, 2H), 3.03-3.06 (m, 6H), 1.98-2.04 (m, 1H), 1.75-1.84 (m, 1H), 1.65-1.73 (m, 1H), 1.57-1.61 (m, 1H). | 433.3 ($C_{14}H_{22}N_6O_8S$) |
| 41. | Boc-NH-CH(2-pyridyl)-CO-NHNH₂ | $H_2N$-CH(2-pyridyl)-CO- | 10.62 (s, 1H), 10.23 (d, 1H), 8.72 (br s, 3H), 8.62 (br s, 1H), 7.94 (t, 1H), 7.76 (dd, 1H), 7.47 (t, 1H), 5.09-5.10 (m, 1H), 4.00 (br s, 1H), 3.84 (br d, 1H), 3.14-3.21 (m, 1H), 2.99 (br d, 1H), 1.94-2.02 (m, 1H), 1.82-1.91 (m, 1H), 1.66-1.76 (m, 1H), 1.57-1.62 (m, 1H). | 413.2 ($C_{19}H_{18}N_6O_7S \cdot CF_3COOH$) |
| 42. | boc-NH-(2-aminothiazol-4-yl)-CO-NHNH₂ | $H_2N$-(2-aminothiazol-4-yl)-CO- | $D_2O$ exchange: 7.33 (s, 1H), 4.00 (br s, 1H), 3.83 (d, 1H), 3.28 (d, 1H), 3.00 (br d, 1H), 2.00-2.05 (m, 1H), 1.76-1.86 (m, 1H), 1.67-1.75 (m, 1H), 1.59-1.64 (m, 1H). | 405.1 ($C_{11}H_{14}N_6O_7S_2$) |

Example-43

Sodium salt of trans-sulfuric acid mono-[2-(N'-(cyano-acetyl)-hydrazinocarbonyl)-7-oxo-1,6-diaza-bicyclo[3.2.1]oct-6-yl]ester Tetrabutylammonium salt of trans-sulfuric acid mono-[2-(N'-(cyano-acetyl)-hydrazinocarbonyl)-7-oxo-1,6-diaza-bicyclo[3.2.1]oct-6-yl]ester (600 mg, obtained using procedure described in Step-1 to Step-3 of Example 1 (using cyano acetic acid hydrazide in the place of (S)—N-tert-butoxycarbonyl-pyrrolidine-2-carboxylic acid hydrazide) was loaded in tetrahydrofuran and water 1:9 mixture (10 ml) and passed slowly through freshly activated Amberlite 200C resin in sodium form (100 gm). The column was eluted with 10% tetrahydrofuran in water mixture. The fractions were analyzed on TLC and desired fractions were evaporated to remove volatile solvent under vacuum below 40° C. The aqueous layer was then washed with dichloromethane (25 ml×2) and layers were separated. The aqueous layer was concentrated under vacuum below 40° C. to provide residue, which was azeotroped with acetone and triturated with diethyl ether to provide a suspension. The suspension was filtered to provide title compound (Sodium salt of trans-sulfuric acid mono-[2-(N'-(2-cyano-acetyl)-hydrazinocarbonyl)-7-oxo-1,6-diaza-bicyclo[3.2.1]oct-6-yl]ester) in 300 mg quantity and in 81% yield.

Analysis: MS (ES−) $C_{10}H_{12}N_5O_7SNa$, 346.2 (M−1) as a free sulfonic acid;

$H^1NMR$ (DMSO-d₆)=10.2 (s, 1H), 10.05 (s, 1H), 3.99 (s, 1H), 3.82 (d, 1H), 3.72 (s, 1H), 3.36 (s, 1H), 3.14 (br d, 1H), 2.99 (d, 1H), 1.98-2.03 (m, 1H), 1.75-1.84 (m, 1H), 1.56-1.72 (m, 2H).

Compounds 44 to 52 (Table 2) were using a procedure described in Example-16 and using corresponding $R_1CONHNH_2$ in the place of cyano acetic acid hydrazide.

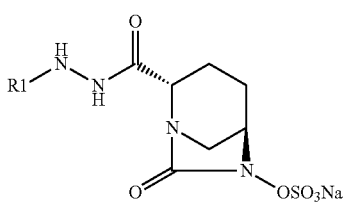

TABLE 2

| Example No. | Acid hydrazide (R₁CONHNH₂) | R₁ | H¹ NMR (DMSO-d₆) | Mass (ES-1) as free acid (MF) |
|---|---|---|---|---|
| 44. | t-Boc—NHNH₂ | t-C₄H₉—O—CO— | 9.70 (s, 1H), 8.71 (s, 1H), 3.98 (s, 1H), 3.73, (d, 1H), 3.13 (d, 1H), 2.97 (br d, 1H), 1.97-2.01 (m, 1H), 1.73-1.83 (m, 1H), 155-2.72 (m, 2H), 1.38 (s, 9H). | 379.3 ($C_{12}H_{19}N_4O_8SNa$) |
| 45. | 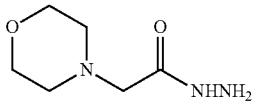 | 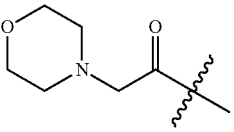 [SMILES: *C(=O)CN1CCOCC1] | 10.02 (br s, 2H), 3.98 (br s, 1H), 3.85 (d, 1H), 3.66-2.70 (m, 4H), 3.37 (br s, 2H), 3.05 (s, 2H), 2.76 (br s, 4H), 2.00-2.04 (m, 1H), 1.73-1.82 (m, 1H), 1.58-1.70 (m, 2H). | 406.3 ($C_{13}H_{20}N_5O_8SNa$) |
| 46. | 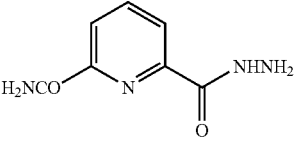 | 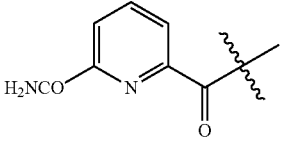 | 11.00 (s, 1H), 10.17 (s, 1H), 8.91 (s, 1H), 8.17-8.20 (m, 3H), 7.74 (s, 1H), 4.04 (br s, 1H), 3.91 (d, 1H), 3.06 (br d, 1H), 1.90-2.06 (m, 2H), 1.77-1.87 (m, 1H), 1.61-1.77 (m, 2H). | 426.9 ($C_{14}H_{15}N_6O_8SNa$) |
| 47. | 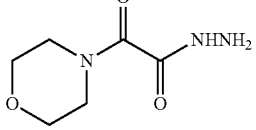 | 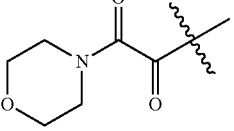 | 10.45 (br s, 1H), 10.08 (br s, 1H), 3.99 (br s, 1H), 3.81 (br d, 1H), 3.56-3.58 (m, 4H), 3.41-3.51 (m, 2H), 2.99-3.10 (m, 2H), 2.06 (br s, 2H) 2.01-2.03 (m, 1H), 2.82-1.83 (m, 1H), 1.59-1.72 (m, 2H). | 419.9 ($C_{13}H_{18}N_5O_9SNa$) |
| 48. | 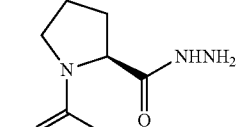 | 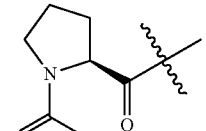 | 9.81 (br s, 1H), 9.69 (br s, 1H), 5.77 (s, 2H), 4.21 (t, 1H), 3.98 (br s, 1H), 3.77 (d, 1H), 3.34-3.38 (m, 1H), 3.16-3.29 (m, 2H), 2.96 (br d, 1H), 1.73-1.98 ( m, 6H), 1.58-1.72 (m, 2H). | 419.2 ($C_{13}H_{19}N_6O_8S•Na$) |
| 49. | 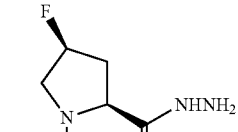 | 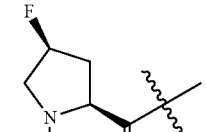 | 9.77 (br s, 2H), 5.95 (s, 2H), 5.32 (s, 0.5H), 5.18 (br s 0.5H), 4.38 (dd, 1H), 3.98 (br s, 1H), 3.81 (d, 1H), 3.35-3.59 (m, 2H), 2.97-3.25 (m, 1H), 2.96 (br d, 1H), 1.99-2.39 (m, 2H), 1.82-1.95 (m, 1H), 1.75-1.82 (m, 1H), 1.59-1.69 (m, 2H). | 437.2 ($C_{13}H_{18}N_6O_8FS•Na$) |
| 50. | 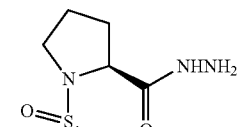 | 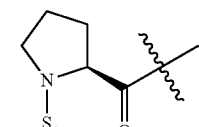 | 9.83 (br s, 2H), 7.32 (s, 1H), 4.21 (dd, 1H), 3.98 (br 1H), 3.77 (d, 1H), 3.38-3.44 (m, 1H), 3.21-3.25 (m, 1H), 2.90-2.98 (m, 4H), 1.56-2.12 (m, 8H). | 454.2 ($C_{13}H_{20}N_5O_9S_2•Na$) |
| 51. | 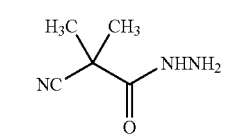 | 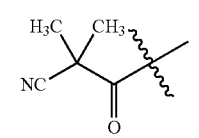 | D₂O exchange: 3.95-4.05 (m, 2H), 3.10-3.19 (m, 1H), 2.95-3.05 (m, 1H), 1.68-1.98 (m, 4H), 1.29 (s, 3H), 1.21 (s, 3H). | 374.2 ($C_{12}H_{16}N_5O_7S•Na$) |
| 52. | 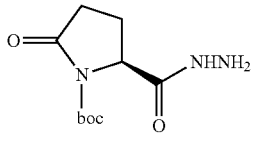 | 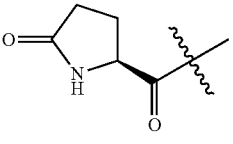 [SMILES: *C(=O)[C@@H]1CCC(=O)N1] | 9.95 (s, 2H), 7.93 (s, 1H), 4.03-4.05 (m, 1H), 3.99 (br s, 1H), 3.81 (d, 1H), 3.19 (d, 1H), 2.98 (br d, 1H), 2.28-2.48 (m, 1H), 1.84-2.25 (m, 5H), 1.56-1.75 (m, 2H). | |

Compounds of the invention from Example 1 to 52 were prepared using (S)-pyrroglutamic acid as a starting compound.
The absolute stereochemistry is therefore (2S, 5R) 7-oxo-1,6-diaza-bicyclo[3.2.1]octane ring.
Thus, the compound of Example-2, trans-sulfuric acid mono-[2-(N'-[(R)-piperidin-3-carbonyl]-hydrazinocarbonyl)-7-oxo-1,6-diaza-bicyclo[3.2.1]oct-6-yl] ester has the absolute stereochemistry as (2S,5R)-sulfuric acid mono-[2-(N'-[(R)-piperidin-3-carbonyl]-hydrazinocarbonyl)-7-oxo-6-diaza-bicyclo[3.2.1]oct-6-yl] ester.
Alternatively, if the starting compound used is (R)-pyrroglutamic_acid the resulting compounds will have (2R, 5S) stereochemistry in 7-oxo-1,6-diaza-bicyclo[3.2.1] octane ring.
A reference to a compound according to the invention also includes corresponding compounds having (2S, 5R) and (2R, 5S) stereochemistry.

Biological Activity

The biological activity of representative compounds according to the invention against various bacterial strains was investigated. In a typical study, overnight grown bacterial cultures were diluted appropriately and inoculated on the agar media containing doubling dilutions of the test compounds. Observation for growth or no growth was performed after 16-20 hours of incubation at 35±2° C. in ambient air. The overall procedure was performed as per Clinical and Laboratory Standards Institute (CLSI) recommendations (Clinical and Laboratory Standards Institute (CLSI), Performance Standards for Antimicrobial Susceptibility Testing, 20th Informational Supplement, M 100-S20, Volume 30, No. 1, 2010). The results of these studies are summarized in Tables 3 to 8.

Table 3 details antibacterial activity of representative compounds according to the invention against various *E. coli* strains (NCTC 13351, M 50 and 7 MP) expressing ESBL (Extended Spectrum Beta Lactamases).

TABLE 3

Antibacterial activity of representative compounds according to the invention (MIC expressed in mcg/ml)

| Sr. | Compound of Example No. | Bacterial Strain | | |
|---|---|---|---|---|
| | | *E. coli* NCTC 13351 | *E. coli* M 50 | *E. coli* 7 MP |
| 1. | 1 | 0.025 | 0.25 | 0.25 |
| 2. | 2 | 0.25 | 0.25 | 1 |
| 3. | 3 | 0.25 | 0.25 | 1 |
| 4. | 4 | 8 | 8 | 16 |
| 5. | 5 | 0.25 | 0.25 | 0.5 |
| 6. | 6 | 32 | 64 | 128 |
| 7. | 7 | 2 | 2 | 4 |
| 8. | 8 | 1 | 1 | 2 |
| 9. | 9 | 1 | 2 | 4 |
| 10. | 10 | 1 | 8 | 32 |
| 11. | 11 | 2 | 1 | 4 |
| 12. | 12 | 1 | 8 | 32 |
| 13. | 13 | 1 | 1 | 2 |
| 14. | 14 | 0.5 | 0.25 | 2 |
| 15. | 15 | 8 | 4 | 16 |
| 16. | 16 | 1 | 1 | 2 |
| 17. | 17 | 0.5 | 0.5 | 2 |
| 18. | 18 | 8 | 4 | 32 |
| 19. | 19 | 1 | 1 | 2 |
| 20. | 20 | 2 | 2 | 8 |
| 21. | 21 | 1 | 1 | 4 |
| 22. | 22 | 4 | 4 | 8 |
| 23. | 23 | 4 | 4 | 8 |
| 24. | 24 | 1 | 1 | 4 |
| 25. | 25 | 1 | 1 | 4 |
| 26. | 26 | 1 | 1 | 2 |
| 27. | 27 | 4 | 2 | 8 |
| 28. | 28 | 1 | 1 | 4 |
| 29. | 29 | 32 | 16 | 128 |
| 30. | 30 | 16 | 8 | 32 |
| 31. | 31 | 1 | 1 | 4 |
| 32. | 32 | 0.5 | 0.5 | 1 |
| 33. | 33 | 1 | 0.5 | 2 |
| 34. | 34 | 2 | 2 | 8 |
| 35. | 35 | 1 | 1 | 4 |
| 36. | 36 | 1 | 1 | 2 |
| 37. | 37 | 2 | 2 | 4 |
| 38. | 38 | 4 | 2 | 8 |
| 39. | 39 | 4 | 2 | 8 |
| 40. | 40 | 1 | 1 | 4 |
| 41. | 41 | 4 | 4 | 16 |
| 42. | 42 | 32 | 32 | 64 |
| 43. | 43 | 1 | 2 | 8 |
| 44. | 44 | 32 | 32 | 64 |
| 45. | 45 | 4 | 8 | 8 |
| 46. | 46 | 32 | 64 | 128 |

TABLE 3-continued

Antibacterial activity of representative compounds according to the invention (MIC expressed in mcg/ml)

| Sr. | Compound of Example No. | Bacterial Strain | | |
|---|---|---|---|---|
| | | *E. coli* NCTC 13351 | *E. coli* M 50 | *E. coli* 7 MP |
| 47. | 47 | 32 | 64 | 128 |
| 48. | 48 | 16 | 8 | 32 |
| 49. | 49 | 32 | 16 | 16 |
| 50. | 50 | 16 | 16 | 32 |
| 51. | 51 | 16 | 16 | 32 |
| 52. | 52 | 0.5 | 0.5 | 2 |

Tables 4 and 5 provide antibacterial activity of representative compounds according to the invention against various Multi Drug Resistant (MDR) Gram-negative bacterial strains expressing various ESBLs. The activities are expressed as MICs (mcg/ml). For comparison, the activity of several known antibacterial agents (for example, Ceftazidime, Aztreonam, Imipenem, Ciprofloxacin and Tigecycline) are also included. As can be seen, the representative compounds according to the invention exhibit antibacterial activity against various MDR strains. The data in Table 4 and 5 also indicates that the compounds according to the invention exhibit potent activity against a wide variety of bacteria, even against those producing different types of beta-lactamase enzymes. In general, the activity of the compounds according to the invention against various beta-lactamase producing bacterial strains is even better than the other antibacterial agents currently employed in the clinical practice to treat such infections.

The antibacterial activity of representative compounds according to the invention was also investigated in combination with at least one antibacterial agent using the above study protocol and the results are given Table 6. As can be seen, the use of compounds according to the invention significantly lowered MIC values of the antibacterial agent (e.g. in this case Ceftazidime). The results also suggest the compounds according the invention increase antibacterial effectiveness of the antibacterial agent when said antibacterial agent is co-administered with a pharmaceutically effective amount of a compound of Formula (I) or a stereoisomer or a pharmaceutically acceptable salt thereof.

The antibacterial activity of representative compounds according to the invention was also investigated in combination with a beta-lactamase inhibitor using the above study protocol and the results are given in Table 7. As can be seen, the compounds according to the invention in combination with a beta lactam inhibitor exhibited excellent antibacterial activity against various bacterial strains. For example, a combination comprising compound of Example 2 (and also Example 3) according to the invention in combination with sulbactam exhibited much superior MIC values compared with when these were used alone. The results also suggest that compounds according to the invention in combination with a beta-lactam inhibitor can be effectively used in preventing or treating a bacterial infection in a subject, including those infections caused by bacteria producing one or more beta-lactamase enzymes.

The antibacterial activity of representative compounds according to the invention was also investigated in combination with a beta-lactamase inhibitor and a antibacterial agent using the above study protocol and the results are given in Table 8. As can be seen, the compounds according to the invention in combination with at least one beta lactam inhibitor and at least one antibacterial agent exhibited excellent antibacterial activity against various bacterial strains. For example, a combination comprising compound of Example 2 (and also Example 3) according to the invention in combination with sulbactam and Cefepime exhibited better MIC values compared with when these were used alone. The results also suggest that compounds according to the invention in combination with at least one beta-lactam inhibitor and at least one antibacterial agent can be effectively used in preventing or treating a bacterial infection in a subject, including those infections caused by bacteria producing one or more beta-lactamase enzymes.

TABLE 4

Comparative antibacterial activity of representative compounds according to the invention against various Multi Drug Resistant (MDR) Gram negative strains (expressed as MICs (mcg/ml).

| | | Class A ESBL | | | Class C ESBL | | | KPC ESBL | | |
|---|---|---|---|---|---|---|---|---|---|---|
| Sr. | Compound | E. Coli W 13353 | E. Coli W 13351 | E. Coli W 13352 | E. Coli M 50 | E. Coli H 484 | E. Coli B 89 | K penumoniae H 521 | K penumoniae H 523 | K penumoniae H 525 |
| 1. | Ceftazidime | 32 | 32 | >32 | >32 | >32 | >32 | >32 | >32 | >32 |
| 2. | Aztreonam | >32 | >32 | >32 | >32 | >32 | >32 | >32 | >32 | >32 |
| 3. | Imipenem | 0.25 | 0.25 | 0.25 | 0.5 | 4 | 0.5 | 16 | 16 | 16 |
| 4. | Ciprofloxacin | >32 | 0.5 | 0.12 | >32 | >32 | >32 | 32 | 8 | 32 |
| 5. | Tigecyclin | 1 | 1 | 0.25 | 0.5 | 0.25 | 0.5 | 2 | 8 | 2 |
| 6. | Example 1 | 0.25 | 0.5 | 0.5 | 0.5 | 2 | 0.5 | 0.5 | 0.5 | 0.5 |
| 7. | Example 2 | 0.12 | 0.25 | 0.25 | 0.25 | 0.12 | 0.25 | 0.5 | 1 | 0.5 |
| 8. | Example 3 | 0.25 | 0.5 | 0.5 | 0.5 | 0.5 | 0.25 | 0.5 | 0.5 | 0.5 |
| 9. | Example 5 | 0.5 | 0.25 | 0.5 | 1 | 1 | 0.5 | 1 | 1 | 2 |
| 10. | Example 7 | 0.5 | 2 | 1 | 2 | 4 | 4 | 2 | 1 | 2 |
| 11. | Example 8 | 1 | 1 | 1 | 1 | 2 | 1 | 1 | 0.5 | 1 |
| 12. | Example 9 | 1 | 1 | 1 | 1 | 2 | 1 | 1 | 0.5 | 0.5 |
| 13. | Example 11 | 2 | 2 | 2 | 2 | 16 | 2 | 4 | 2 | 2 |
| 14. | Example 13 | 1 | 1 | 2 | 1 | 4 | 1 | 1 | 0.5 | 1 |
| 15. | Example 14 | 0.5 | 0.5 | 0.5 | 0.5 | 2 | 0.5 | 0.5 | 0.25 | 0.25 |
| 16. | Example 17 | 0.25 | 0.5 | 0.5 | 0.5 | 4 | 0.5 | 0.5 | 0.5 | 0.5 |
| 17. | Example 19 | 2 | 2 | 2 | 2 | 4 | 1 | 1 | 1 | 1 |
| 18. | Example 30 | 8 | 16 | 16 | 8 | 8 | 8 | 8 | 8 | >32 |
| 19. | Example 35 | 1 | 1 | 1 | 1 | 1 | 1 | 2 | 1 | 1 |
| 20. | Example 38 | 2 | 4 | 4 | 2 | 8 | 2 | 2 | 2 | 2 |
| 21. | Example 43 | 1 | 1 | 1 | 1 | 8 | 1 | 2 | 1 | 1 |

TABLE 5

Comparative antibacterial activity of representative compounds according to the invention against various Multi Drug Resistant (MDR) Gram negative strains (expressed as MICs (mcg/ml).

| | | Class B ESBL | | | P. aeruginosa | | |
|---|---|---|---|---|---|---|---|
| Sr. | Compound | K. penumoniae S 48 | E. Coli M 3 | E. Coli M 44 | ATCC 27853 | Ps 21 | Ps 32 |
| 1. | Ceftazidime | >32 | >32 | >32 | 1 | >32 | >32 |
| 2. | Aztreonam | >32 | >32 | >32 | 2 | 8 | 8 |
| 3. | Imipenem | 16 | 8 | 32 | 4 | >32 | >32 |
| 4. | Ciprofloxacin | >32 | >32 | >32 | 0.5 | 32 | 0.12 |
| 5. | Tigecyclin | 1 | 4 | 0.25 | 16 | 16 | 16 |
| 6. | Example 1 | 2 | 1 | 0.25 | 16 | 16 | 32 |
| 7. | Example 2 | 0.5 | 2 | 0.5 | 8 | 8 | 8 |
| 8. | Example 3 | 0.5 | 0.5 | 0.12 | 2 | 4 | 4 |
| 9. | Example 5 | 2 | 1 | 0.5 | >32 | >32 | >32 |
| 10. | Example 7 | 4 | 4 | 2 | >32 | >32 | >32 |
| 11. | Example 8 | 1 | 4 | 0.5 | 8 | 16 | 8 |
| 12. | Example 9 | 1 | 2 | 0.5 | 8 | 8 | 16 |
| 13. | Example 11 | 2 | 8 | 1 | >32 | >32 | >32 |
| 14. | Example 13 | 1 | 1 | 1 | 32 | 32 | 16 |
| 15. | Example 14 | 4 | 0.5 | 0.25 | 8 | 16 | 8 |
| 16. | Example 17 | 0.5 | 0.5 | 0.5 | >32 | >32 | >32 |
| 17. | Example 19 | 4 | 1 | 1 | 32 | >32 | >32 |
| 18. | Example 30 | >32 | 8 | 16 | >32 | >32 | >32 |
| 19. | Example 35 | 2 | 1 | 2 | >32 | >32 | 32 |
| 20. | Example 38 | 4 | 1 | 4 | >32 | >32 | >32 |
| 21. | Example 43 | 1 | 4 | 0.5 | >32 | >32 | >32 |

TABLE 6

Antibacterial activity of Ceftazidime in presence of representative compounds of the invention against various Multi Drug Resistant (MDR) Gram negative strains.

| | | Ceftazidime MIC (expressed in mcg/ml) | |
|---|---|---|---|
| Sr. | Composition | K. pneumoniae ATCC 700603 (ESBL type: Class A) | P. vulgaris S-137B (ESBL type: Class C) |
| 1. | Ceftazidime alone | >32 | >32 |
| 2. | Ceftazidime + Compound of Example 1 (4 mcg/ml) | 0.06 | 1 |
| 3. | Ceftazidime + Compound of Example 2 (4 mcg/ml) | 0.06 | 1 |
| 4. | Ceftazidime + Compound of Example 3 (4 mcg/ml) | 0.06 | 1 |
| 5. | Ceftazidime + Compound of Example 5 (4 mcg/ml) | 0.25 | 4 |
| 6. | Ceftazidime + Compound of Example 8 (4 mcg/ml) | 0.06 | 0.5 |
| 7. | Ceftazidime + Compound of Example 9 (4 mcg/ml) | 0.12 | 1 |
| 8. | Ceftazidime + Compound of Example 14 (4 mcg/ml) | 0.03 | 0.5 |

Note:
The MICs of each of compounds of Example 1, 2, 3, 5, 8, 9 and 14 when used alone (in the absence of Ceftazidime) is >32 mcg/ml.

TABLE 7

Antibacterial activity of sulbactam in combination with a compound according to the invention.

| | | MIC of sulbactam (expressed in mcg/ml) | | | |
|---|---|---|---|---|---|
| Sr. | Composition | A. baumannii J-143 | A. baumannii 1460648 | A. baumannii S-334 | A. baumannii G-165 |
| 1. | Sulbactam alone | 32 | 32 | 32 | 32 |
| 2. | Sulbactam + compound of Example 2 (4 mcg/ml) | 4 | 4 | 4 | 2 |
| 3. | Sulbactam + compound of Example 2 (8 mcg/ml) | 4 | 4 | 2 | 2 |
| 4. | Sulbactam + compound of Example 3 (4 mcg/ml) | 8 | 4 | 8 | 2 |
| 5. | Sulbactam + compound of Example 3 (8 mcg/ml) | 1 | 2 | 4 | 2 |

Standalone MIC of compound of Example 2 and Example 3 for each of the strains was >32 mcg/ml.

TABLE 8

Antibacterial activity of an antibacterial agent in combination with sulbactam and a compound according to the invention.

| | | MIC of Cefepime (expressed in mcg/ml) | | | |
|---|---|---|---|---|---|
| Sr. | Composition | A. baumannii J-143 | A. baumannii 1460648 | A. baumannii S-334 | A. baumannii G-165 |
| 1. | Cefepime alone | >32 | >32 | 32 | >32 |
| 2. | Cefepime + compound of Example 2 (4 mcg/ml) | >32 | 32 | 32 | >32 |
| 3. | Cefepime + compound of Example 2 (8 mcg/ml) | 32 | 32 | 32 | 32 |
| 4. | Cefepime + Sulbactam (4 mcg/ml) | 16 | 32 | 16 | 16 |
| 5. | Cefepime + Sulbactam (8 mcg/ml) | 16 | 16 | 8 | 8 |
| 6. | Cefepime + Sulbactam (8 mcg/ml) + compound of Example 2 (4 mcg/ml) | 0.25 | 0.25 | 0.25 | 0.25 |
| 7. | Cefepime + Sulbactam (8 mcg/ml) + compound of Example 2 (8 mcg/ml) | 0.25 | 0.25 | 0.25 | 0.25 |
| 8. | Cefepime + compound of Example 3 (4 mcg/ml) | >32 | 32 | 32 | >32 |
| 9. | Cefepime + compound of Example 3 (8 mcg/ml) | 32 | 32 | 32 | 32 |
| 10. | Cefepime + Sulbactam (8 mcg/ml) + compound of Example 3 (4 mcg/ml) | 0.12 | 0.12 | 0.12 | 0.12 |
| 11. | Cefepime + Sulbactam (8 mcg/ml) + compound of Example 3 (8 mcg/ml) | 0.06 | 0.06 | 0.06 | 0.06 |

Standalone MIC of sulbactam for each of the strains was 32 mcg/ml.
Standalone MIC of compound of Example 2 and Example 3 for each of the stains was >32 mcg/ml.

The invention claimed is:

1. A pharmaceutical composition comprising: (a) cefepime or a pharmaceutically acceptable derivative thereof, and (b) a compound which is trans-sulfuric acid mono-[2-(N'—[(R)-piperidin-3-carbonyl]-hydrazinocarbonyl)-7-oxo-1,6-diaza-bicyclo[3.2.1]oct-6-yl]ester or a stereoisomer or a pharmaceutically acceptable salt thereof.

2. A pharmaceutical composition comprising: (a) cefepime or a pharmaceutically acceptable derivative thereof, and (b) a compound which is trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester or a stereoisomer or a pharmaceutically acceptable salt thereof.

3. A pharmaceutical composition according to claim 1, further comprising sulbactam or a pharmaceutically acceptable salt thereof.

4. A pharmaceutical composition according to claim 2, further comprising sulbactam or a pharmaceutically acceptable salt thereof.

5. A method for treating a bacterial infection in a subject, said method comprising administering to said subject a pharmaceutical composition according to any one of claims 1 to 4.

6. A method for treating bacterial infection in a subject, said method comprising administering to said subject a pharmaceutically effective amount of: (a) cefepime or a pharmaceutically acceptable derivative thereof, and (b) a compound which is trans-sulfuric acid mono-[2-(N'—[(R)-piperidin-3-carbonyl]-hydrazinocarbonyl)-7-oxo-1,6-diaza-bicyclo[3.2.1]oct-6-yl]ester or a stereoisomer or a pharmaceutically acceptable salt thereof.

7. A method for treating bacterial infection in a subject, said method comprising administering to said subject a pharmaceutically effective amount of: (a) cefepime or a pharmaceutically acceptable derivative thereof, and (b) a compound which is trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester or a stereoisomer or a pharmaceutically acceptable salt thereof.

8. A method for increasing antibacterial effectiveness of cefepime or pharmaceutically acceptable derivative thereof in a subject, said method comprising co-administering cefepime or a pharmaceutically acceptable derivative thereof with a compound which is trans-sulfuric acid mono-[2-(N'—[(R)-piperidin-3-carbonyl]-hydrazinocarbonyl)-7-oxo-1,6-diaza-bicyclo[3.2.1]oct-6-yl]ester or a stereoisomer or a pharmaceutically acceptable salt thereof.

9. A method for increasing antibacterial effectiveness of cefepime or a pharmaceutically acceptable derivative thereof in a subject, said method comprising co-administering cefepime or a pharmaceutically acceptable derivative thereof with a compound which is trans-sulfuric acid mono-[2-(N'—[(R)-pyrrolidin-3-carbonyl]-hydrazinocarbonyl)-7-oxo-1,6-diaza-bicyclo[3.2.1]oct-6-yl]ester or a stereoisomer or a pharmaceutically acceptable salt thereof.

* * * * *